(12) United States Patent
van Hoek et al.

(10) Patent No.: US 12,384,821 B2
(45) Date of Patent: Aug. 12, 2025

(54) ANTIMICROBIAL PEPTIDES AND COMPOSITIONS, METHODS, ARTICLES AND KITS RELATING THERETO

(71) Applicant: George Mason University, Fairfax, VA (US)

(72) Inventors: Monique L. van Hoek, Centreville, VA (US); Barney M. Bishop, Annandale, VA (US)

(73) Assignee: George Mason University, Fairfax, VA (US)

(*) Notice: Subject to any disclaimer, the term of this patent is extended or adjusted under 35 U.S.C. 154(b) by 0 days.

(21) Appl. No.: 17/393,495

(22) Filed: Aug. 4, 2021

(65) Prior Publication Data

US 2022/0041666 A1 Feb. 10, 2022

Related U.S. Application Data

(60) Provisional application No. 63/061,559, filed on Aug. 5, 2020.

(51) Int. Cl.
| | | |
|---|---|---|
| *C07K 14/46* | (2006.01) |
| *A61L 15/32* | (2006.01) |
| *C07K 7/08* | (2006.01) |
| *G01N 33/569* | (2006.01) |
| *A61K 38/00* | (2006.01) |

(52) U.S. Cl.
CPC ............ *C07K 14/463* (2013.01); *A61L 15/32* (2013.01); *C07K 7/08* (2013.01); *G01N 33/56911* (2013.01); *A61K 38/00* (2013.01); *G01N 2400/50* (2013.01)

(58) Field of Classification Search
CPC ......... C07K 14/463; C07K 7/08; A61L 15/32; G01N 33/56911; G01N 2400/50; A61K 38/00
See application file for complete search history.

(56) References Cited

U.S. PATENT DOCUMENTS

| | | | |
|---|---|---|---|
| 8,071,540 B2 * | 12/2011 | Montelaro ........... | A61K 38/162 |
| | | | 514/3.3 |
| 10,633,420 B2 | 4/2020 | Bishop et al. | |
| 2020/0172570 A1 | 6/2020 | Bishop et al. | |
| 2020/0190156 A1 | 6/2020 | Bishop et al. | |
| 2020/0270307 A1 * | 8/2020 | Del'Guidice ......... | C12N 15/90 |

FOREIGN PATENT DOCUMENTS

| | | |
|---|---|---|
| CN | 101265296 A | 9/2008 |
| WO | 2010148079 A1 | 12/2010 |
| WO | 2018022875 A1 | 2/2018 |

OTHER PUBLICATIONS

Kem A. Sochacki, Real-time attack on single *Escherichia coli* cells by the human antimicrobial peptide LL-37, PNAS, Apr. 19, 2011 I vol. 108, No. 16, E77-E81.*
Basu, Polysaccharide-Based Conjugates for Biomedical Applications, Bioconjugate Chem. 2015, 26, 1396-1412).*
Monique L. van Hoek et al., "The Komodo dragon (*Varanus komodoensis*) genome and identification of innate immunity genes and clusters", BMC Genomics, 2019, 18 pages, 20:684.
Barney M. Bishop et al., "Discovery of Novel Antimicrobial Peptides from *Varanus komodoensis* (Komodo Dragon) by Large-Scale Analyses and De-Novo-Assisted Sequencing Using Electron-Transfer Dissociation Mass Spectrometry", J. Proteome Res., 2017, 16, 13 pp. 1470-1482.
Samantha J. Hitt et al., "Komodo-dragon cathelicidin-inspired peptides areantibacterial against carbapenem-resistant Klebsiella pneumoniae", Journal of Medical Microbiology, Oct. 21, 2020, 3 pages, vol. 69, Issue 11.
Cathelicidin-B1-like, Jun. 24, 2020, 2 pages.

* cited by examiner

*Primary Examiner* — Lianko G Garyu
*Assistant Examiner* — Erinne R Dabkowski
(74) *Attorney, Agent, or Firm* — Raj S. Dave; Davé Law Group, LLC

(57) ABSTRACT

Peptides are described herein, in particular peptides having antimicrobial properties, as are compositions, articles, and kits comprising such peptides, and methods for using the peptides.

20 Claims, 7 Drawing Sheets

Specification includes a Sequence Listing.

ANTIMICROBIAL PEPTIDES AND COMPOSITIONS, METHODS, ARTICLES AND KITS RELATING THERETO

CROSS-REFERENCE TO RELATED APPLICATION

This application claims the benefit under 35 U.S.C § 119 of U.S. Provisional Application No. 63/061,559, titled as "ANTIMICROBIAL PEPTIDES AND COMPOSITIONS, METHODS, ARTICLES & KITS RELATING THERETO", filed on Aug. 5, 2020, which is hereby incorporated by reference in its entirety.

GOVERNMENT INTERESTS

This invention was made with government support under Grant No. HDTRA1-12-C-0039 awarded by the Defense Threat Reduction Agency. The government has certain rights in the invention.

REFERENCE TO SEQUENCE LISTING

The Sequence Listing concurrently submitted herewith as a text file named "7074_0108PUS1_Sequence_Listing.txt," created on Jul. 28, 2020, and having a size of 4,636 bytes is herein incorporated by reference pursuant to 37 C.F.R. § 1.52(e)(5). A revised sequence listing is submitted as .txt file. The contents of the electronic sequence listing (GMUN_025_01 US.txt; Size: 4.73 K B; and Date of Creation: Jun. 18, 2023) herein incorporated by reference in its entirety. In the revised sequence listing created on Jun. 18, 2023, includes an additional LLRRFG as SEQ ID NO:12. There is no change in the other 11 sequences listed in the sequence listing created on Jul. 28, 2020.

FIELD OF THE INVENTION

The present invention relates to peptides comprising antimicrobial properties, to compositions, kits, and articles of manufacture comprising such peptides, as well as to methods for using the peptides.

BACKGROUND

Many currently available antimicrobial agents are not effective in the treatment of pathogens including single- or multi-drug resistant pathogens. Therefore, the search for new therapeutics with antimicrobial properties is considered a pressing need.

For Example, *Klebsiella pneumoniae* is a Gram-negative rod-shaped bacterium belonging to the family Enterobacteriaceae, and it has been associated with a range of human diseases, including urinary tract infections, bacteremia and pneumonia, both in community and hospital-associated infections. *K. pneumoniae* has also been shown to cause pyogenic liver abscesses. It is a member of the ESKAPE family of pathogens, a group of bacteria that are responsible for the majority of nosocomial infections. Moreover, many strains of ESKAPE pathogens are multidrug resistant (MDR), and they are thus of particular concern. Of particular concern are carbapenem-resistant strains of Enterobacteriaceae, which are considered one of the most urgent threats. Carbapenem-resistant enterobacteriaceae (CRE) are associated with 9000 infections and 600 deaths annually in the US, with 7900 infections being linked to CRE *K. pneumoniae* specifically.

There is a need for new and effective antimicrobial agents as well as therapeutic, prophylactic, and/or diagnostic methods and strategies that target microbial organisms.

SUMMARY OF THE INVENTION

In one aspect, the present invention provides a peptide comprising:

```
                                        (SEQ ID NO: 1)
(a) FRWRRFFRKAKRFLKRHGVSIAIGTVRLLRRFG;

(SEQ ID NO: 2)
(b) RRWRRFFQKAKRFVKRHGVSIAVGAYRIIG;
``` or
(c) the amino acid sequence of SEQ ID NO:1 or 2 with one or more substitutions, insertions, additions, or deletions;
wherein the peptide optionally further has a modification at an N- and/or C-terminus of the peptide.

In another aspect, the present invention provides a peptide comprising:
(a) the amino acid sequence set forth in Formula (I) (SEQ ID NO:3):

FRWRRFFRKAKRFLKRH
Xaa18VSIAIGTVRLLRRFG wherein Xaa18 is any amino acid, with the proviso that Xaa18 is not glycine (G); or
(b) the amino acid sequence set forth in Formula (I) (SEQ ID NO:3) with one or more substitutions, insertions, additions, or deletions.

In some aspects, the present invention provides a peptide comprising:
(a) the amino acid sequence set forth in Formula (II) (SEQ ID NO:5):

Xaa1RWRRFFXaa8KAKRXaa13Xaa14Xaa15Xaa16Xaa17Xaa18 wherein independently of each other:
Xaa1 is phenylalanine (F) or arginine (R);
Xaa8 is glutamine (Q) or arginine (R);
Xaa13 is leucine (L) or isoleucine (I);
Xaa14 is leucine (L) or isoleucine (I);
Xaa15 is arginine (R) or glycine (G);
Xaa16 is arginine (R) or absent;
Xaa17 is phenylalanine (F) or absent; and
Xaa18 is glycine (G) or absent; or
(b) the amino acid sequence set forth in Formula (II) (SEQ ID NO:5) with one or more substitutions, insertions, additions, or deletions.

In another aspect, the present invention provides a polynucleotide encoding a peptide of the present invention.

In other aspects, the present invention provides a composition comprising a peptide of the present invention or a polynucleotide encoding the peptide.

In some aspects, the present invention provides an article of manufacture comprising a peptide of the present invention.

In one aspect, the present invention provides a kit comprising a peptide of the present invention or a polynucleotide encoding the peptide.

In another aspect, the present invention provides a method for treating infection by a microbial organism in a subject. The method comprises administering to the subject a peptide of the present invention or a polynucleotide encoding the peptide.

In other aspects, the present invention provides a method for preventing, reducing or inhibiting growth of a microbial organism or biofilm on a surface. The method comprises contacting the surface with a composition comprising a peptide of the present invention.

In some aspects, the present invention provides a method for promoting wound healing in a subject. The method comprises administering to the subject a peptide of the present invention or a polynucleotide encoding the peptide.

In one aspect, the present invention provides a method for treating or preventing endotoxemia in a subject. The method comprises administering to the subject an amount of a peptide of the present invention, or a polynucleotide encoding the peptide, effective to treat or prevent endotoxemia in the subject.

In another aspect, the present invention provides a method for determining lipopolysaccharide (LPS) in a sample. The method comprises contacting the sample a peptide of the present invention under a condition such that the LPS binds to the peptide to form a complex; and detecting the complex.

In some aspects, the present invention provides a method for diagnosing an LPS-associated disorder in a subject. The method comprises forming a complex between LPS and a peptide of the present invention under a condition such that the LPS binds to the peptide to form the complex; and detecting the complex.

In other aspects, the present invention provides a method for treating a composition comprising LPS. The method comprises contacting the composition with a peptide of the present invention under a condition such that the LPS binds to the peptide to form a complex; and separating the complex from the composition, thereby reducing or eliminating the LPS from the composition.

BRIEF DESCRIPTION OF THE DRAWINGS

DRGN-6 refers to SEQ ID NO:6, DRGN-7 refers to SEQ ID NO:6 with N-terminus acetylated, DRGN-8 refers to SEQ ID NO:7, NACATH refers to SEQ ID NO:9.

DETAILED DESCRIPTION OF THE INVENTION

Figure 1A:
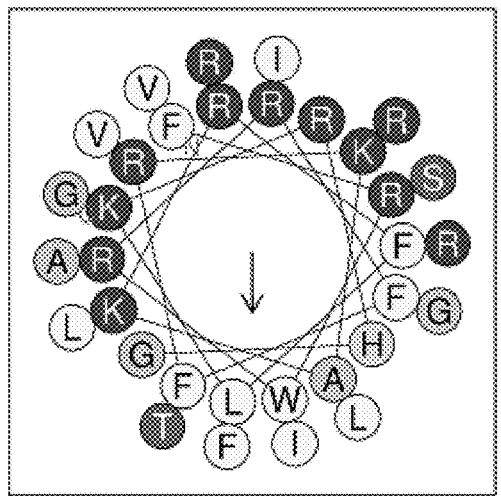
FIGS. 1A-1E shows predicted secondary structures and helical wheel diagrams of (A) VK-CATH-4.1 (SEQ ID NO:1); (B) VK-CATH-4.2 (SEQ ID NO:2); (C) DRGN-6 (SEQ ID NO:6); (D) DRGN-8 (SEQ ID NO:7); and (E) DRGN-10 (SEQ ID NO:8). Structures were predicted by I-TASSER and highest rated PDB file was visualized using Chimera (Yang, J. et al., The I-TASSER Suite: protein structure and function prediction, Nat Meth. 2015; 12(1):7-8; Pettersen, E. F. et al., UCSF Chimera—a visualization system for exploratory research and analysis, Journal of computational chemistry, 2004; 25(13):1605-12).
Figure 1A:
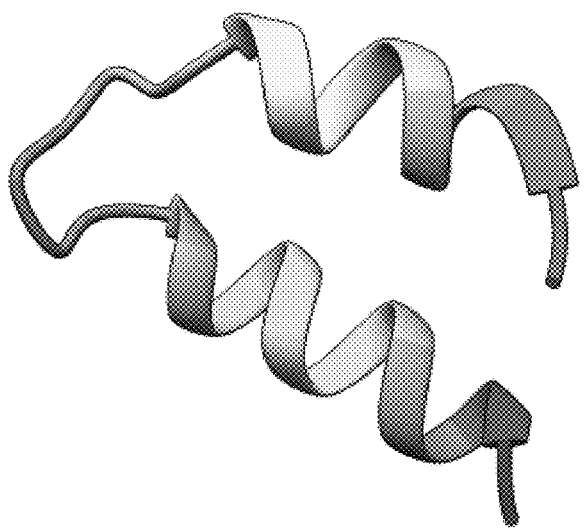

Disclosed herein are peptides, as well as compositions, methods, articles, and kits related to peptides, including antimicrobial peptides (AMPs), and strategies for leveraging the therapeutic and/or prophylactic potential thereof. According to various aspects and embodiments, the peptides, compositions, methods, articles, and kits provided herein can be used, among other things, for therapeutic and/or prophylactic treatment and/or prevention of an infections, wounds and/or biofilms, including infections, wounds and/or biofilms that involve a microbial organism including, but not limited to, a microbial organism that may be classified or otherwise characterized as a biodefense and/or drug- or multidrug-resistant/tolerant pathogen.

In some embodiments, the microbial organism is a bacterium, virus, fungus, or protozoa.

In one embodiment, the bacterium is a Gram-negative or Gram-positive bacterium.

In another embodiment, the bacterium is of the genus $Klebsiella,$ $Francisela,$ $Acinetobacter,$ $Pseudomonas,$ $Escherichia,$ $Haemophilus,$ $Proteus,$ $Enterobacter,$ $Serratia,$ $Burkholderia,$ $Stenotrophomonas,$ $Alcaligenes,$ $Mycobacterium,$ $Legionella,$ $Neisseria,$ $Yersinia,$ $Shigella,$ $Vibrio,$ or $Salmonella.$ In other embodiments, the bacterium is $Klebsiella$ $pneumoniae,$ $Klebsiella$ $oxytoca,$ $Francisela$ $tularensis,$ $Acinetobacter$ $baumannii,$ $Pseudomonas$ $aeruginosa,$ $Escherichia$ $coli,$ $Haemophilus$ $influenzae,$ $Proteus$ $mirabilis,$ $Enterobacter$ $species,$ $Serratia$ $marcescens,$ $Burkholderia$ $cepacia,$ $Stenotrophomonas$ $maltophilia,$ $Alcaligenes$ $xylosoxidans,$ $Mycobacterium$ $tuberculosis,$ $Neisseria$ $gonorrhoeae,$ $Yersinia$ $pestis,$ $Shigella$ $dysenteriae,$ $Vibrio$ $cholera,$ or $Salmonella$ $typhi.$ In one embodiment, the bacterium is $Francisela$ $tularensis,$ $Francisela$ $novicida,$ $Francisela$ $hispaniensis,$ $Francisela$ $noatunensis,$ $Francisela$ $philomiragia,$ $Francisela$ $halioticida,$ $Francisela$ $endociliophora,$ $Francisela$ $guangzhouensis,$ or $Francisela$ $piscicida.$ In another embodiment, the bacterium is $Klebsiella$ $pneumoniae.$ In other embodiments, the bacterium is of the genus $Staphylococcus,$ $Bacillus,$ $Rhodococcus,$ $Actinobacteria,$ $Lactobacillus,$ $Actinomyces,$ $Clostridium,$ or $Streptococcus.$ In some embodiments, the bacterium is $Staphylococcus$ $aureus,$ $Bacillus$ $anthracis,$ $Streptococcus$ $mutans$ or $Streptococcus$ $sanguinis.$ In other embodiments, viruses include but are not limited to influenza virus, parainfluenza virus, respiratory syncytial virus, human metapneumovirus, corona virus family members, human immunodeficiency virus, herpes simplex virus, cytomegalovirus, SARS (Severe Acute Respiratory Syndrome) virus, and Epstein-Barr virus.

In some embodiments, fungi include but are not limited to *Histoplasma capsulatum, Coccidioides immitis, Blastomyces dermatitidis, Paracoccidioides brasiliensis, Candida* sp., *Aspergillus* sp., *Mucor* sp., *Cryptococcus neoformans*.

In other embodiments, protozoa include but are not limited to *Entamoeba, Acanthamoeba, Balamuthia, Leishmania, Trypanosoma, Trichomonas, Lophomonas, Cryptosporidium, Cyclospora, Toxoplasma, Plasmodium, Babesia, Encephalitozoon, Enterocytozoon* and *Balantidium*.

Subjects that can be administered or otherwise benefit from the peptides, compositions, methods, articles, and kits provided herein include vertebrates such as, without limitation, mammals. A mammal can be a human or animal including livestock and companion animals.

Companion animals include but are not limited to animals kept as pets. Examples of companion animals include cats, dogs, and horses, as well as birds, such as parrots and parakeets. Livestock refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys.

In some embodiments, the subject is a human. In another embodiment, the subject is a non-human mammal.

In other embodiments, the subject can be a human who is a medical patient (e.g., a diabetes patient, or a patient in a hospital, clinic), a member of the armed services or law enforcement, a fire fighter, or a worker in the gas, oil, or chemical industry. In one embodiment, the subject is an animal that is a veterinarian subject/patient (e.g., livestock or companion animal).

In some aspects, the present invention provides a peptide comprising:

(SEQ ID NO: 1)
(a) FRWRRFFRKAKRFLKRHGVSIAIGTVRLLRRFG;

(SEQ ID NO: 2)
(b) RRWRRFFQKAKRFVKRHGVSIAVGAYRIIG;

or (c) the amino acid sequence of SEQ ID NO:1 or 2 with one or more substitutions, insertions, additions, or deletions;

wherein the peptide optionally further has a modification at an N- and/or C-terminus of the peptide.

In some embodiments, the peptide further has the modification at the N- and/or C-terminus of the peptide.

In one embodiment, the modification at the N-terminus of the peptide is an acetylation.

In another embodiment, the modification at the C-terminus of the peptide is an amidation.

In some embodiment, the modification at the N-terminus of the peptide is an acetylation and the modification at the C-terminus of the peptide is an amidation.

In other aspects, the present invention provides a peptide comprising:

(a) the amino acid sequence set forth in Formula (I) (SEQ ID NO:3):

FRWRRFFRKAKRFLKRHX$_{aa18}$VSIAIGTVRLLRRFG wherein X$_{aa18}$ is any amino acid, with the proviso that X$_{aa18}$ is not glycine (G); or (b) the amino acid sequence set forth in Formula (I) (SEQ ID NO:3) with one or more substitutions, insertions, additions, or deletions.

In one embodiment, Xaa18 in Formula (I) (SEQ ID NO:3) is alanine (A).

In one embodiment, the peptide comprises the amino acid sequence:

(SEQ ID NO: 4)
(a) FRWRRFFRKAKRFLKRHAVSIAIGTVRLLRRFG;

or (b) the amino acid sequence of SEQ ID NO:4 with one or more substitutions, insertions, additions, or deletions with the proviso that position X$_{aa18}$ is alanine (A).

In other aspects, the present invention provides a peptide comprising:

(a) the amino acid sequence set forth in Formula (II) (SEQ ID NO:5):

X$_{aa1}$RWRRFFX$_{aa8}$KAKRX$_{aa13}$X$_{aa14}$X$_{aa15}$X$_{aa16}$X$_{aa17}$X$_{aa18}$ wherein independently of each other:

X$_{aa1}$ is phenylalanine (F) or arginine (R);

X$_{aa8}$ is glutamine (Q) or arginine (R);

X$_{aa13}$ is leucine (L) or isoleucine (I);

X$_{aa14}$ is leucine (L) or isoleucine (I);

X$_{aa15}$ is arginine (R) or glycine (G);

X$_{aa16}$ is arginine (R) or absent;

X$_{aa17}$ is phenylalanine (F) or absent; and

X$_{aa18}$ is glycine (G) or absent; or (b) the amino acid sequence set forth in Formula (II) (SEQ ID NO:5) with one or more substitutions, insertions, additions, or deletions.

In one embodiment, in Formula (II), Xaa1 is arginine (R), Xaa8 is glutamine (Q), Xaa13 is leucine (L), Xaa14 is leucine (L), Xaa15 is arginine (R), Xaa16 is arginine (R), Xaa17 is phenylalanine (F), and Xaa18 is glycine (G).

In one embodiment, in Formula (II), Xaa1 is arginine (R), Xaa8 is arginine (R), Xaa13 is leucine (L), Xaa14 is leucine (L), Xaa15 is arginine (R), Xaa16 is arginine (R), Xaa17 is phenylalanine (F), and Xaa18 is glycine (G).

In one embodiment, in Formula (II), Xaa1 is arginine (R), Xaa8 is arginine (R), Xaa13 is isoleucine (I), Xaa14 is isoleucine (I), Xaa15 is glycine (G), Xaa16 is absent, Xaa17 is absent, and Xaa18 is absent.

In one embodiment, the peptide comprises the amino acid sequence:

(SEQ ID NO: 6)
(a) RRWRRFFQKAKRLLRRFG;

or (b) the amino acid sequence of SEQ ID NO:6 with one or more substitutions, insertions, additions, or deletions with the proviso that position X$_{aa1}$ is arginine (R), X$_{aa8}$ is glutamine (Q), X$_{aa13}$ is leucine (L), X$_{aa14}$ is leucine (L), X$_{aa15}$ is arginine (R), X$_{aa16}$ is arginine (R), X$_{aa17}$ is phenylalanine (F), and X$_{aa18}$ is glycine (G).

In one embodiment, the peptide comprises the amino acid sequence:

(a) RRWRRFFRKAKRLLRRFG;  (SEQ ID NO: 7)

or (b) the amino acid sequence of SEQ ID NO:7 with one or more substitutions, insertions, additions, or deletions with the proviso that position $X_{aa1}$ is arginine (R), $X_{aa8}$ is arginine (R), $X_{aa13}$ is leucine (L), $X_{aa14}$ is leucine (L), $X_{aa15}$ is arginine (R), $X_{aa16}$ is arginine (R), $X_{aa17}$ is phenylalanine (F), and $X_{aa18}$ is glycine (G).

In one embodiment, the peptide comprises the amino acid sequence:

(a) RRWRRFFRKAKRIIG;  (SEQ ID NO: 8)

or (b) the amino acid sequence of SEQ ID NO:8 with one or more substitutions, insertions, additions, or deletions with the proviso that position $X_{aa1}$ is arginine (R), $X_{aas}$ is arginine (R), $X_{aa13}$ is isoleucine (I), $X_{aa14}$ is isoleucine (I), and $X_{aa15}$ is glycine (G).

In other embodiments, the peptide comprises the amino acid sequence of SEQ ID NO:1, 2, 3, 4, 5, 6, 7, or 8.

In some embodiments, the peptides provided herein can be shorter, longer, or variant versions of any one of SEQ ID NOs:1-8, including without limitation peptides having one or more substitutions and/or insertions relative to any one of SEQ ID NOs:1-8. In other embodiments, the peptides have one or more biological activities (e.g., antimicrobial).

The term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

In one embodiment, relates to a peptide of the present invention comprising a sequence that is selected from the group consisting of SEQ ID NO: 1 to SEQ ID NO: 8 or a variant thereof, which is at least 75%, at least 80%, at least 85%, at least 90% homologous to SEQ ID NO: 1 to SEQ ID NO: 8.

In some embodiments, the peptides provided herein can include one or more (e.g., one, two, three, four, five or more) substitutions, insertions, deletions, and/or additions (and combinations thereof) as compared to the sequence set forth in any one of SEQ ID NOs:1-8.

Amino acid substitutions can be conservative or non-conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Non-conservative amino acid substitutions typically entail exchanging a member of one of the classes described above for a member of another class. After making an amino acid substitution, insertion, deletion, and/or addition, the activity of a peptide containing the amino acid substitution, insertion, deletion, or addition can be assessed using the assays described herein.

In other embodiments, the peptides provided herein have a length of about 10 amino acids to about 50 amino acids. For example, in some embodiments, a peptide can have a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In other embodiments, a peptide can have a length of, without limitation, about 10 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, about 45 to about 50 amino acids, about 10 to about 20 amino acids, about 20 to about 30 amino acids, about 30 to about 40 amino acids, or about 40 to about 50 amino acids.

In one embodiment, the amino acid sequence of the peptide has a length of 15 to 33 amino acids. In another embodiment, the amino acid sequence of the peptide has a length of 15 amino acids. In some embodiments, the amino acid sequence of the peptide has a length of 18 amino acids. In one embodiment, the amino acid sequence of the peptide has a length of 30 amino acids.

In still other embodiments, the amino acid sequence of the peptide has a length of 33 amino acids.

In one embodiment, the peptide comprises the sequence of SEQ ID NO:1, wherein the peptide has a length of 33 amino acids.

In another embodiment, the sequence of the peptide consists of the sequence as set forth in SEQ ID NO:1.

In some embodiments, the sequence of the peptide consists essentially of the sequence as set forth in SEQ ID NO:1.

In one embodiment, the peptide comprises the sequence of SEQ ID NO:2, wherein the peptide has a length of 30 amino acids.

In another embodiment, the sequence of the peptide consists of the sequence as set forth in SEQ ID NO:2.

In some embodiments, the sequence of the peptide consists essentially of the sequence as set forth in SEQ ID NO:2.

In one embodiment, the peptide comprises the sequence of SEQ ID NO:3, wherein the peptide has a length of 33 amino acids.

In another embodiment, the sequence of the peptide consists of the sequence as set forth in SEQ ID NO:3.

In some embodiments, the sequence of the peptide consists essentially of the sequence as set forth in SEQ ID NO:3.

In one embodiment, the peptide comprises the sequence of SEQ ID NO:4, wherein the peptide has a length of 33 amino acids.

In another embodiment, the sequence of the peptide consists of the sequence as set forth in SEQ ID NO:4.

In some embodiments, the sequence of the peptide consists essentially of the sequence as set forth in SEQ ID NO:4.

In one embodiment, the peptide comprises the sequence of SEQ ID NO:5, wherein the peptide has a length of 18 amino acids.

In another embodiment, the sequence of the peptide consists of the sequence as set forth in SEQ ID NO:5.

In some embodiments, the sequence of the peptide consists essentially of the sequence as set forth in SEQ ID NO:5.

In one embodiment, the peptide comprises the sequence of SEQ ID NO:6, wherein the peptide has a length of 18 amino acids.

In another embodiment, the sequence of the peptide consists of the sequence as set forth in SEQ ID NO:6.

In some embodiments, the sequence of the peptide consists essentially of the sequence as set forth in SEQ ID NO:6.

In one embodiment, the peptide comprises the sequence of SEQ ID NO:7, wherein the peptide has a length of 18 amino acids.

In another embodiment, the sequence of the peptide consists of the sequence as set forth in SEQ ID NO:7.

In some embodiments, the sequence of the peptide consists essentially of the sequence as set forth in SEQ ID NO:7.

In one embodiment, the peptide comprises the sequence of SEQ ID NO:8, wherein the peptide has a length of 15 amino acids.

In another embodiment, the sequence of the peptide consists of the sequence as set forth in SEQ ID NO:8.

In some embodiments, the sequence of the peptide consists essentially of the sequence as set forth in SEQ ID NO:8.

In other embodiments, a peptide of the present invention has a modification at an N- and/or C-terminus of the peptide. In some embodiments, the peptide has a modification at the N-terminus and at the C-terminus.

In another embodiment, the peptide comprises the amino acid sequence of SEQ ID NO:1, 2, 3, 4, 5, 6, 7, or 8, wherein the peptide further has a modification at an N- and/or C-terminus of the peptide.

For example, as known in the art, peptides can be derivatized by chemical alterations such as amidation, acylation, glycosylation, sulfation, phosphorylation, acetylation, and cyclization.

Such chemical alterations may be obtained through chemical or biochemical methodologies, as well as through in vivo processes, or any combination thereof.

For example, N-terminal α-amines can be either neutral or positively charged depending on the surrounding pH and chemical modifications. In one embodiment, the peptide terminal modification comprises Na-acetylation e.g., catalyzed by N-acetyl-transferases. N-acetyl-transferases also have the ability to formylate and propionylate N-termini. For example, pyroglutamate forms through cyclization of N-terminal glutamine or glutamate, either spontaneously or enzymatically by glutaminyl cyclases. Palmitoylation and myristoylation can occur at free N-terminal glycines, and N-terminal cysteines can be palmitoylated (S-palmitoylation) at their side chain. N-terminal mono-, di- and tri-methylation modifications are other example.

In other embodiment, C-terminal α-amidation may be present. In some embodiments, such modifications can neutralize the negative charge of the carboxyl group at the C-terminus. In other embodiments, C-terminal modification is C-methyl-esterification.

In some embodiments, the modification of a peptide of the present invention at the N- or C-terminus reduces susceptibility to proteolytic degradation of the modified peptide as compared to the unmodified peptide.

In one embodiment, the modification at the N-terminus of the peptide is an acetylation.

In another embodiment, the modification at the C-terminus of the peptide is an amidation.

In some embodiment, the modification at the N-terminus of the peptide is an acetylation and the modification at the C-terminus of the peptide is an amidation.

In one embodiment, the peptide of any one of SEQ ID NOs:1-8 has a modification at an N- and/or C-terminus.

In one embodiment, the modification at the N-terminus of the peptide of any one of SEQ ID NOs:1-8 comprises acetylation.

In another embodiment, the modification at the C-terminus of the peptide of any one of SEQ ID NOs:1-8 comprise amidation.

In some embodiment, the modification at the N-terminus of the peptide of any one of SEQ ID NOs:1-8 is acetylation and the modification at the C-terminus of the peptide is amidation.

In another embodiment, the peptide comprises the sequence of any one of SEQ ID NOs:1-8, wherein the N-terminus is acetylated.

In one embodiment, the peptide comprises the sequence of any one of SEQ ID NOs:1-8, wherein the C-terminus is amidated.

In another embodiment, the peptide comprises the sequence of any one of SEQ ID NOs:1-8, wherein the N-terminus is acetylated, and wherein the C-terminus is amidated.

In some embodiments, the peptide comprises the sequence of SEQ ID NO:1, wherein the N-terminus is acetylated.

In other embodiments, the peptide comprises the sequence of SEQ ID NO:1, wherein the C-terminus is amidated.

In one embodiment, the peptide comprises the sequence of SEQ ID NO:1, wherein the N-terminus is acetylated, and wherein the C-terminus is amidated.

In some embodiments, the peptide comprises the sequence of SEQ ID NO:2, wherein the N-terminus is acetylated.

In other embodiments, the peptide comprises the sequence of SEQ ID NO:2, wherein the C-terminus is amidated.

In one embodiment, the peptide comprises the sequence of SEQ ID NO:2, wherein the N-terminus is acetylated, and wherein the C-terminus is amidated.

In some embodiments, the peptide comprises the sequence of SEQ ID NO:3, wherein the N-terminus is acetylated.

In other embodiments, the peptide comprises the sequence of SEQ ID NO:3, wherein the C-terminus is amidated.

In one embodiment, the peptide comprises the sequence of SEQ ID NO:3, wherein the N-terminus is acetylated, and wherein the C-terminus is amidated.

In some embodiments, the peptide comprises the sequence of SEQ ID NO:4, wherein the N-terminus is acetylated.

In other embodiments, the peptide comprises the sequence of SEQ ID NO:4, wherein the C-terminus is amidated.

In one embodiment, the peptide comprises the sequence of SEQ ID NO:4, wherein the N-terminus is acetylated, and wherein the C-terminus is amidated.

In some embodiments, the peptide comprises the sequence of SEQ ID NO:5, wherein the N-terminus is acetylated.

In other embodiments, the peptide comprises the sequence of SEQ ID NO:5, wherein the C-terminus is amidated.

In one embodiment, the peptide comprises the sequence of SEQ ID NO:5, wherein the N-terminus is acetylated, and wherein the C-terminus is amidated.

In some embodiments, the peptide comprises the sequence of SEQ ID NO:6, wherein the N-terminus is acetylated.

In other embodiments, the peptide comprises the sequence of SEQ ID NO:6, wherein the C-terminus is amidated.

In one embodiment, the peptide comprises the sequence of SEQ ID NO:6, wherein the N-terminus is acetylated, and wherein the C-terminus is amidated.

In some embodiments, the peptide comprises the sequence of SEQ ID NO:7, wherein the N-terminus is acetylated.

In other embodiments, the peptide comprises the sequence of SEQ ID NO:7, wherein the C-terminus is amidated.

In one embodiment, the peptide comprises the sequence of SEQ ID NO:7, wherein the N-terminus is acetylated, and wherein the C-terminus is amidated.

In some embodiments, the peptide comprises the sequence of SEQ ID NO:8, wherein the N-terminus is acetylated.

In other embodiments, the peptide comprises the sequence of SEQ ID NO:8, wherein the C-terminus is amidated.

In one embodiment, the peptide comprises the sequence of SEQ ID NO:8, wherein the N-terminus is acetylated, and wherein the C-terminus is amidated.

The term "amino acid" as used herein refers to natural amino acids, unnatural amino acids, and amino acid analogs, all in their various stereoisomers (e.g., D and L stereoisomers or other allostereomers if their structures so allow). Natural (or "naturally-occurring") amino acids include the 20 "standard" amino acids that are encoded by the codons of the universal genetic code (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), as well as other "non-standard" amino acids that occur naturally but are not encoded by the codons of the universal genetic code (e.g., hydroxyproline, selenomethionine, and norleucine). Amino acids that are non-standard and/or non-naturally occurring include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native peptides but differs in composition such that either the C-terminal carboxy group, the N-terminal amino group, or the side-chain functional group has been chemically modified or replaced with another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, The Peptides: Analysis, Synthesis, Biology, Academic Press, Inc., New York (1983).

The stereochemistry of a peptide can be described in terms of the topochemical arrangement of the side chains of the amino acid residues about the peptide backbone, which is defined by the peptide bonds between the amino acid residues and the I-carbon atoms of the bonded residues. In addition, peptide backbones have distinct termini and thus direction. The majority of naturally occurring amino acids are L-amino acids (including the 20 standard amino acids as well as a number of other naturally-occurring, non-standard amino acids), and naturally occurring, ribosomally-produced peptides are largely comprised of L-amino acids. D-amino acids are the enantiomers of L-amino acids. Assembling peptides out of D-amino acids, which are not recognized by proteases, can enable evasion from digestion and remain intact until reaching membranes (Wade et al., Proc Natl Acad Sci USA 87(12):4761-4765, 1990).

The peptides provided herein can be made up of L-amino acids, D-amino acids, or a combination thereof. For example, in some embodiments, a peptide can have an amino acid composition in which at least about 10% (e.g., at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%) of the amino acids are D-amino acids. It is to be noted that some amino acid residues have more than one stereocenter, and the peptides provided herein can, in some embodiments, include diastereomers of these amino acids that differ from each other only in the configuration of one of their stereocenters.

In one embodiment, the peptide comprises one or more D-amino acid residues. In some embodiments, at least about 25 percent, illustratively, about 25 to 100 percent, about 50 to about 55 percent, and about 60 to about 75 percent of the amino acids in the peptide can be D-amino acids. In one embodiment, at least about 25 percent of the amino acids in the peptide can be D-amino acids. In another embodiment, 50 percent of the amino acids in the peptide can be D-amino acids. In one embodiment, at least about 75 percent of the amino acids in the peptide can be D-amino acids. In another embodiment, 100 percent of the amino acids in the peptide can be D-amino acids.

In some embodiments, peptidomimetic compounds can be used in place of the peptides provided herein. As used herein, the term "peptidomimetic" refers to compounds that are synthetic, non-peptide compounds having a three-dimensional conformation (a "peptide motif") that is substantially the same as the three-dimensional conformation of a selected peptide; a peptidomimetic compound therefore can essentially reproduce elements of amino acid structural properties and can confer the same or similar function as the selected peptide. As compared to a selected peptide, a peptidomimetic compound includes non-naturally occurring modifications, such as an altered backbone and/or non-natural amino acids. In some embodiments, for example, peptidomimetics can include beta-amino acids, peptoids, and/or N-methyl amino acids.

Peptidomimetic compounds can include amide ("peptide") or non-amide ("non-peptide") bonds in their backbone structure or can include a combination of peptide and non-peptide bonds in their backbone structure. Peptidomimetic compounds that are protease resistant or that have additional characteristics that enhance therapeutic utility, such as increased cell permeability and prolonged biological half-life, can be particularly useful. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, sulfonamide, reduced carbonyl, dimethylene and ketomethylene) can be useful substitutes for peptide bonds in the construction of peptidomimetic compounds. In some embodiments, the compounds provided herein include hybrids that contain one or more peptide portions and one or more peptidomimetic portions. Such hybrid peptides can incorporate a combination of natural amino acids and mimetic amino acids (e.g., standard amino acids and peptoids) in the same molecule.

The peptides provided herein can be obtained by any of a number of methods, including those known in the art. In some embodiments, a peptide can be obtained by extraction from a natural source (e.g., from isolated cells, tissues or bodily fluids), or can be produced by expression of a recombinant nucleic acid encoding the peptide, or by chemical synthesis (e.g., using solid phase peptide synthesis methods or a peptide synthesizer such as an ABI Peptide Synthesizer; Applied Biosystems; Foster City, CA). For example, standard recombinant technology using an expression vector encoding a peptide disclosed herein can be used. The resulting peptide then can be purified using, for example, affinity chromatographic techniques and HPLC. The extent of purification can be measured by any appropriate method, including but not limited to: column chromatography, polyacrylamide gel electrophoresis, or high-performance liquid chromatography.

In some embodiments, a peptide can be designed or engineered to contain a tag sequence that allows the peptide to be purified (e.g., captured onto an affinity matrix). For example, a tag such as c-myc, hemagglutinin, polyhistidine, or FLAG™ tag (Kodak) can be used to aid peptide purification. Such tags can be inserted anywhere within the peptide, including at either the carboxyl or amino terminus. Other fusions that can be used include enzymes that aid in the detection of the peptide, such as alkaline phosphatase. In some embodiments, a peptide can be amidated at its carboxy terminus.

In some embodiments, a peptide disclosed herein can be isolated or purified. A "purified peptide" is a peptide that either has no naturally occurring counterpart (e.g., a peptidomimetic), or has been chemically synthesized and is thus uncontaminated by other peptides, or has been recombinantly produced and has been separated from components of the cell in which it was produced, or that has been separated or purified from other cellular components by which it is naturally accompanied (e.g., other cellular proteins, polynucleotides, or cellular components). Typically, a peptide is considered "purified" when it is at least 70%, by dry weight, free from the proteins and other molecules with which it naturally associates. A preparation of a purified peptide therefore can be, for example, at least about 80%, at least about 90%, or at least about 99%, by dry weight, the peptide. Suitable methods for purifying peptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

In one aspect, the present invention provides a polynucleotide encoding a peptide disclosed herein, or a nucleic acid molecule (e.g., expression vector, plasmid, etc.) comprising the polynucleotide encoding the peptide.

In other aspects, the activities of the peptides provided herein can be tested using any of a number of suitable methods, including those described in the Examples herein.

An activity of a peptide against bacteria, for example, can be tested by culturing the bacteria in a suitable liquid medium until cells reach a desired density (e.g., OD600 of 0.8 to 1.1), and then diluting the cells to a suitable concentration in buffer containing varying concentrations of one or more selected peptides. Peptide concentrations used in the assays can range from 0 μg/ml to about 100 μg/ml with intermediate concentrations (e.g., about 0.01 μg/ml, about 0.05 μg/ml, about 0.1 μg/ml, about 0.5 μg/ml, about 1 μg/ml, about 2.5 μg/ml, about 5 μg/ml, about 7.5 μg/ml, about 10 μg/ml, about 25 μg/ml, about 50 μg/ml, 75 μg/ml, about 0.01 μg/ml to about 0.1 μg/ml, about 0.05 μg/ml to about 0.5 μg/ml, about 0.1 to about 1 μg/ml, about 0.5 μg/ml to about 5 μg/ml, about 2.5 μg/ml to about 10 μg/ml, or any other range between about 0.01 μg/ml and about 100 μg/ml) that vary for each peptide in order to maximize the number of data points. Assay cultures can be incubated for a desired length of time (e.g., about two hours), and serial dilutions of each sample can be prepared and plated. After a suitable length of incubation, colonies can be counted to determine the effectiveness of the peptide(s).

Bacterial survival at each peptide concentration can be calculated according to the ratio of the number of colonies on the plates corresponding to the peptide concentration and the average number of colonies observed for assay cultures lacking peptide. The peptide concentration required to kill about 50% of the viable cells in the assay cultures (EC50) can be determined by plotting percent survival as a function of the log of peptide concentration (log μg/ml) and fitting the data to Equation (1) using, for example, GraphPad Prism (GraphPad Software, Inc., San Diego, CA), which describes a sigmoidal dose-response.

$$S=SB+((ST-SB)/(1+10(\text{Log EC50}-X)H)) \quad (1)$$

In Equation (1), S is percent survival, ST and SB represent the upper and lower survival boundaries, X is the log of the peptide concentration, and H is the Hill slope of the transition region.

Another form for Equation (1) is:

$$Y=\text{Bottom}+((\text{Top}-\text{Bottom})/(1+10[(\log EC50-X)*\text{Hill Slope}])) \quad (1)$$

where Y corresponds to bacterial survival (in percentage) at a given peptide concentration (g/ml), with X being the logarithm of that concentration. In the equation, "Top" and "Bottom" refer to the upper and lower boundaries and were constrained to values <100% and >0%, respectively.

Analysis of the efficacy of antimicrobials utilizing in vivo models can also be conducted prior to clinical trials. For example, a mammalian animal model can be employed in order to test the in vivo capabilities of antimicrobials; however, alternative models may be appropriate for screening of lead antimicrobial candidates (EC50 activity <10 µg/ml). *Galleria mellonella*, the greater wax moth, can be an alternative model that is relatively easy to obtain and has a system of antimicrobial protection similar to that of mammals. These factors make larvae of *G. mellonella* a good model of infection for various pathogenic microorganisms (Propst, C. N., et al., Front Microbiol, 2016. 7: p. 696; Sprynski, N., et al., Methods Mol Biol, 2014. 1197: p. 3-9; Aperis, G., et al., Microbes Infect, 2007. 9(6): p. 729-34; Blower, R. J., et al., Virulence, 2017: p. 1-7). *G. mellonella* has been previously used as an infection model for in vivo effect of antimicrobial peptides and antibiotics against *Francisella* spp. Infections (Propst, C. N., et al., Front Microbiol, 2016. 7: p. 696; Aperis, G., et al., Microbes Infect, 2007. 9(6): p. 729-34).

In some embodiments, to evaluate the ability of selected antimicrobial peptide to prolong survival of infected *G. mellonella*, larvae can be infected (e.g., with *K. pneumonia* live vaccine strain (LVS)) and then treated with a single dose of e.g., 10 ng of a peptide. Improved survival of *G. mellonella* treated with selected peptide when compared to untreated group(s) can be indicative of in vivo capabilities of antimicrobials.

The effect of a peptide on biofilm production can be assessed by, for example, incubating a biofilm-forming bacteria or other microbe with varying concentrations of one or more peptides for a certain length of time (e.g., 24 hours at 37° C.). Optical density of the cultures (e.g., at OD600 nm) can be measured to assess microbial growth, and cultures then can be stained with crystal violet to assess biofilm production. See, e.g., Durham-Colleran et al., Microb Ecol 59(3):457-465, 2010.

An endotoxin neutralizing activity of a peptide can be assessed by, for example, the ability of the peptide to inhibit *E. coli* LPS in a rabbit pyrogenicity test or to increase the lethal dose 50 (LD50) of *E. coli* LPS in mouse (e.g., CD1 mouse).

In another aspect, the present invention provides a composition comprising a peptide, or a polynucleotide encoding the peptide, provided herein.

For example, peptides as provided herein can be formulated in compositions by admixture with one or more pharmaceutically acceptable, non-toxic excipients or carriers. Such compositions can be used to treat or prevent microbial infection, for example. In some embodiments, a composition can include one particular peptide, while in other embodiments a composition can include two or more different peptides (e.g., peptides having different sequences or different amounts of D- and L-amino acids). In some embodiments, the compositions provided herein can contain one or more peptides at a concentration of about 0.001 µg/ml to about 100 µg/ml (e.g., about 0.001 µg/ml to about 0.01 µg/ml, about 0.005 µg/ml to about 0.05 µg/ml, about 0.01 µg/ml to about 1 µg/ml, about 0.01 µg/ml to about 10 µg/ml, about 0.05 µg/ml to about 5 µg/ml, about 0.05 µg/ml to about 25 µg/ml, about 0.1 µg/ml to about 10 µg/ml, about 0.5 µg/ml to about 50 µg/ml, about 1 µg/ml to about 100 µg/ml, or about 10 µg/ml to about 100 µg/ml.

In some embodiments, the composition further comprises an excipient. Excipients (also referred to as pharmaceutically acceptable carriers) can be liquid or solid and can be selected with the planned manner of administration in mind so as to provide for the desired bulk, consistency, and other pertinent transport and chemical properties, when combined with one or more of peptides and any other components of a given composition. Common excipients include, without limitation, sterile water, saline, polyalkylene glycols such as polyethylene glycol, oils of vegetable origin, hydrogenated naphthalenes, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some embodiments, biocompatible, biodegradable lactide polymer, lactide/glycolide copolymer, polyoxethylene-polyoxypropylene copolymers, or combinations thereof can be used as excipients for controlling the release of a peptide in vivo.

In other embodiments, a composition can include a peptide and one or more molecular crowding agents such as, by way of example and not limitation, FICOLL™ (e.g., FICOLL™ 70), polyethylene glycol (PEG), and dextran. FICOLL™ is a neutral, highly branched, high-mass, hydrophilic polysaccharide that dissolves readily in aqueous solutions. PEG is a polymer of ethylene oxide and is commercially available over a wide range of molecular weights from 300 g/mol to 10,000,000 g/mol. Dextran is a complex, branched polysaccharide made of glucose molecules. Without being bound by a particular mechanism, such agents may help to mimic the natural cellular environment, which may enhance the activity of the peptide. Such agents can be included in the compositions in amounts from about 5% to about 50% wt/vol (e.g., about 5%, about 10%, about 15%, about 20%, about 25%, about 30%, about 35%, about 40%, about 45%, or about 50% wt/vol, or any range there between, including about 5% to about 10%, about 10% to about 20%, about 20% to about 25%, about 25% to about 30%, about 30% to about 40%, or about 40% to about 50%).

In some embodiments, compositions can further include one or more other peptides, wherein each of the one or more other peptides has one or more biological activities (e.g., antimicrobial activity). In one embodiment, the one or more other peptides include, but are not limited to, one or more cathelicidins. Cathelicidins are known to one of ordinary skill in the art to refer to a large and diverse collection of cationic antimicrobial peptides, for example as described in U.S. Patent Publication No. 2012-0149631 A1, which is herein incorporated by reference in its entirety.

In one embodiment, compositions also can include one or more conventional antibiotics (e.g., amoxicillin, cephalexin, bacteriocin, neomycin, and/or polymyxin) and/or active ingredients from wound dressings or wound treatment compositions (e.g., NEOSPORIN®, bacitracin, and silver sulfadiazine).

Compositions can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations).

Compositions for other routes of administration also can be prepared as desired using appropriate methods. In addition, compositions can be prepared for in vitro use (e.g., for use on environmental surfaces or on medical devices).

Formulations for topical administration of peptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets.

Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

In other embodiments, the composition is a pharmaceutical composition.

In some embodiments, pharmaceutical compositions can include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety.

Emulsion formulations can be useful for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidyl-choline, dimyristoyl phosphatidylglycerol, or dioleoyl phosphatidylethanolamine. Numerous lipophilic agents are commercially available, including LIPOFECTIN® (Invitrogen/Life Technologies, Carlsbad, CA) and EFFECTENE™ (Qiagen, Valencia, CA).

The peptides provided herein further encompass pharmaceutically acceptable salts, esters, or salts of such esters, or any other compound which, upon administration to an animal including a human, is capable of providing (directly or indirectly) the biologically active metabolite or residue thereof. Accordingly, for example, provided herein are pharmaceutically acceptable salts of peptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the peptides described herein (i.e., salts that retain the desired biological activity of the parent peptide without imparting undesired toxicological effects). Examples of pharmaceutically acceptable salts include, without limitation, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., acetic acid, citric acid, oxalic acid, palmitic acid, or fumaric acid).

Compositions additionally can contain other adjunct components such as, for example, lubricants, preservatives, stabilizers, wetting agents, emulsifiers, salts for influencing osmotic pressure, buffers, colorings, flavorings, and aromatic substances. When added, however, such materials should not unduly interfere with the biological activities of the peptide components within the compositions provided herein. The formulations can be sterilized if desired.

Dosing of compositions for administration to a subject typically is dependent on the severity and responsiveness of the condition to be treated, with the course of treatment lasting, in some embodiments, from several days to several months, or in other embodiments until a cure is affected or a diminution of the condition is achieved. Persons of ordinary skill in the art routinely determine optimum dosages, dosing methodologies and repetition rates. Optimum dosages can vary depending on the relative potency of individual peptides and can generally be estimated based on EC50 found to be effective in in vitro and in vivo animal models.

In some embodiments, dosage is about 0.01 µg to about 100 g per kg of body weight, and may be given once or more daily, biweekly, weekly, monthly, or even less often. Following successful treatment, it may be desirable to have the patient undergo maintenance therapy to prevent the recurrence of the disease state.

In some embodiments, a preliminary dosage for human infection can be inferred using guidelines put forth by the FDA (Guidance for Industry: Estimating the Maximum Safe Starting Dose in Initial Clinical Trials for Therapeutics in Adult Healthy Volunteers F.a.D. Administration, Editor. 2005 (Rockville, MD), which is herein incorporated by reference in its entirety).

In one embodiment, dosage is at least about 0.01 mg per kg of body weight, illustratively, about 0.01 mg to about 100 mg per kg of body weight, about 0.05 mg to about 50 mg per kg of body weight, about 0.1 mg to about 10 mg per kg of body weight, about 0.4 mg to about 5 mg per kg of body weight, and may be given once or more daily, biweekly, weekly, monthly, or even less often.

In some embodiments, dosage is about 0.4 mg to about 5 mg per kg of body weight, and may be given once or more daily, biweekly, weekly, monthly, or even less often.

In other embodiments, a dose of at least about 0.01 µg is given, illustratively, about 0.01 µg to about 1 g, about 0.1 µg to about 0.1 g, about 1 µg to about 24 mg, and may be given once or more daily, biweekly, weekly, monthly, or even less often.

In other embodiments, treatments may differ if a subject is resistant or suspected of being resistant to certain antibiotics. For example, if a subject has an infection that is resistant to antibiotics, the dose may be increased, or the treatment may include two or more different peptides.

In other embodiments, one or more peptides can be admixed, encapsulated, conjugated or otherwise associated with other molecules, molecular structures, conventional antibiotics, or mixtures of compounds such as, for example, liposomes, polyethylene glycol, receptor targeted molecules, or oral, topical or other formulations, for assisting in uptake, distribution, absorption, or activity.

In still another aspect, the present invention provides an article of manufacture comprising a peptide as provided herein. In one embodiment, the article is a hygiene product (e.g., a personal hygiene product including but not limited to mouthwash and body wash). In another embodiment, the article is a wound dressing.

In some embodiments, the article is an invasive device, wherein the peptide is covalently or non-covalently attached onto a surface of the device. Covalent and non-covalent methods for attaching peptides to various surfaces are known in the art. In one embodiment, the device is a surgical tool. In another embodiment, the device is an implant. In other embodiments, the device is a catheter, a staple, a suture, an implant, or a tubing.

In still other aspects, the present invention provides a kit comprising a peptide disclosed herein or a polynucleotide encoding the peptide. In one embodiment, the kit further comprises instructions for using the components contained therein.

In another aspect, the present invention provides a method for treating infection by a microbial organism in a subject. The method comprises administering to the subject a peptide disclosed herein or a polynucleotide encoding the peptide. In one embodiment, the peptide comprises the amino acid sequence of SEQ ID NO:1, 2, 3, 4, 5, 6, 7, or 8.

In some embodiments, the infection includes but is not limited to infections of the gastrointestinal tract, respiratory system, circulatory system, lymphatic system, urinary system, muscular system, skeletal system, nervous system, and reproductive system.

In another embodiment, a method for treating an infection by a microbial organism is provided, where the method includes contacting the microbial organism with a peptide or composition as provided herein. In other embodiments, after the contacting step, growth of the microbial organism can be reduced by at least about 5 percent, illustratively, about 5 percent to 100 percent, about 10 percent to about 99.99 percent, about 20 percent to about 95 percent, about 30 percent to about 80 percent, about 40 percent to about 70 percent, and about 50 to about 60 percent when measured in an assay to measure colony formation. In some embodiments, after the contacting, growth of the microbial organism can be reduced by at least about 50 percent when measured in an assay to measure colony formation.

In other embodiments, the infection can be a polymicrobial infection.

In some embodiments, for example, a peptide or a composition comprising the peptide as described herein can be used to treat a subject having a microbial (e.g., bacterial or fungal) infection, such as in a wound that is in or on a subject (e.g., a mammal such as, without limitation, a human). Wounds can result from accidental occurrences, or can result from, for example, medical procedures.

In some embodiments, the subject can be a human who is a medical patient (e.g., a diabetes patient, or a patient in a hospital, clinic, or veterinary setting), a member of the armed services or law enforcement, a fire fighter, or a worker in the gas, oil, or chemical industry. In one embodiment, the subject is an animal suitable to be treated by a veterinarian including, but not limited to pets and livestock/farm animals.

In other aspects, the present invention provides a method for preventing, reducing or inhibiting growth of a microbial organism or biofilm on a surface. The method comprises contacting the surface with a composition comprising a peptide disclosed herein. In one embodiment, the peptide comprises the amino acid sequence of SEQ ID NO:1, 2, 3, 4, 5, 6, 7, or 8.

In one embodiment, the surface is an environmental surface. In another embodiment, the surface is on a prosthetic or an implant. In other embodiments, the surface is in a living organism (e.g., a human or a non-human animal). In some embodiments, the peptides and compositions described herein are used in surface coatings for medical devices (e.g., catheters, prosthetics, implants, and other indwelling devices), or in dressings to be applied to a wound on or in a patient.

Biofilms are aggregates of microorganisms in which cells adhere to each other on a surface.

Without wishing to be bound by any particular theory, it is believed that the adherent cells frequently are embedded in a self-produced matrix of extracellular polymeric substance (EPS) that generally is composed of extracellular DNA, proteins, and polysaccharides. Biofilms are ubiquitous, and can form on virtually any non-shedding, living or non-living surface in a non-sterile aqueous (or very humid) environment. Biofilms can be found, for example, in natural, industrial, hospital, and veterinary settings. Biofilms can be involved in a wide variety of microbial infections in the body, including common problems such as urinary tract infections, catheter infections, ear infections, formation of dental plaque, gingivitis, coating contact lenses, and less common but more serious conditions such as endocarditis, infections in cystic fibrosis, and infections of permanent indwelling devices such as joint prostheses and heart valves. Bacterial biofilms also can impair cutaneous wound healing and reduce topical antibacterial efficiency in healing or treating infected skin wounds.

Chronic opportunistic infections in immunocompromised patients and the aging population are a major challenge for medical professionals, as traditional antibiotic therapies usually are not sufficient to eradicate the infections. One reason for their persistence seems to be the capability of the bacteria to grow within biofilms that protect them from adverse environmental factors.

*Pseudomonas aeruginosa* is an example of an opportunistic pathogen and a causative agent of emerging nosocomial infections. Other examples of microbes that can form medically relevant biofilms include, without limitation, *Streptococcus mutans* and *Streptococcus sanguinis*, which are involved in formation of dental plaque, *Legionella* bacteria, and *Neisseria gonorrhoeae*, which can form biofilms on human cervical epithelial cells.

In some embodiments, after the contacting, growth of the biofilm can be reduced by at least about 5 percent, compared to a control, when measured in an assay to measure optical density. In other embodiments, after the contacting, growth of the biofilm is reduced by at least about 25 percent, compared to a control when measured in an assay to measure optical density.

In other aspects, the present invention provides a method for promoting wound healing in a subject. The method comprises administering to the subject a peptide disclosed herein. In one embodiment, the peptide comprises the amino acid sequence of SEQ ID NO:1, 2, 3, 4, 5, 6, 7, or 8.

In some embodiments, the peptides and compositions described herein can be used in methods for promoting healing of wounds that are not infected (or that show no evidence of infection). For example, in some embodiments, a peptide or composition comprising one or more peptides described herein can be useful for treating an uninfected wound in a subject (e.g., a vertebrate such as a human), for example such that the wound has increased numbers of keratinocytes, shrinks in size more rapidly, and/or heals more quickly than it would without administration of the peptide or composition. In some embodiments, treatment of an uninfected wound with a peptide or composition can be considered effective if the wound size is reduced by at least about 5% (e.g., at least about 10%, at least about 20%, at least about 25%, at least about 30%, at least about 40%, at least about 50%, at least about 60%, at least about 70%, at least about 75%, at least about 80%, at least about 90%, or at least about 95%) during or after treatment, as compared to a control (e.g., a time point before or earlier in the treatment).

In one aspect, the peptides and compositions also can be used in methods that include determining whether a subject having a microbial infection is resistant to one or more conventional antibiotics (e.g., methicillin), or is suspected of being resistant to one or more conventional antibiotics. If the subject is determined to be resistant to the one or more conventional antibiotics or is suspected of being resistant to the one or more conventional antibiotics, the subject can be treated with a peptide or composition provided herein. In contrast, if the subject is determined not to be resistant to the one or more conventional antibiotics or is not suspected of being resistant to the one or more conventional antibiotics, the subject can be treated with the one or more conventional antibiotics. In such methods, the subject can be monitored to determine whether the treatment is effective, and the treatment can be adjusted accordingly. For example, if the subject is treated with one or more conventional antibiotics but is subsequently determined to be resistant to the conventional antibiotic(s), the subject can be treated with a peptide or composition as provided herein. In some embodiments, the subject can be treated with one or more AMPs and conventional antibiotics contemporaneously (e.g., in cases of severe infection insufficient time to try one or the other treatments).

In another aspect, the peptides and compositions provided herein can be used in methods for improving the effectiveness of treatment for microbial infection. For example, a method can include administering to a subject an amount of a peptide or composition that is sub-anti-microbial but is effective to reduce biofilm levels or inhibit biofilm formation or administering a peptide under conditions that are sub-anti-microbial but are effective to reduce biofilm levels or inhibit biofilm formation. For example, a peptide may be less effective as an anti-microbial agent under high salt conditions (e.g., about 125 to about 150 mM salt, including about 130 mM, about 135 mM, about 140 mM, or about 145 mM salt), but can retain effectiveness as an anti-biofilm agent under such conditions. After one or more sub-anti-microbial treatments, the subject can be treated with an anti-microbial amount of the peptide or composition, with the peptide under conditions that are anti-microbial, or with one or more conventional antibiotics. The sub-anti-microbial and anti-microbial treatments can be separated by any length of time, ranging from an hour or less to several hours to a day or more (e.g., about 0.5 hour, about one hour, about two hours, about three hours, about four hours, about six hours, about 12 hours, about 1 day, or more than 1 day).

Treatments can be repeated as needed or desired.

The effectiveness of a peptide or composition containing one or more peptides as described herein can be determined by assessing microbial growth or biofilm growth before, during, and/or after treatment. In some embodiments, for example, samples can be obtained from a subject before treatment, and at one or more different time points during or after treatment with a peptide or composition as provided herein, and microbial growth can be measured by counting the number of colonies that grow up from the samples after they are plated on a solid medium. Biofilm growth can be measured based on optical density (e.g., at 600 nm) and/or staining with crystal violet, for example. Treatment with a peptide or composition can be considered effective if microbial growth or biofilm formation is reduced by at least about 5% (e.g., at least about 10%, at least about 20%, at least about 25%, at least about 30%, at least about 40%, at least about 50%, at least about 60%, at least about 70%, at least about 75%, at least about 80%, at least about 90%, or at least about 95%) during or after treatment, as compared to a control (e.g., a time point before or earlier in the treatment).

Lipopolysaccharide (LPS) is a major structural component of the Gram-negative bacterial outer membrane and is believed to protect bacteria from antimicrobial compounds. LPS from *E. coli* and other Gram-negative bacteria is the endotoxin and, for example, may activate innate immunity through binding TLR4 receptors. Administration of parenteral products contaminated with pyrogens including LPS may lead to, for example, development of fever, induction of inflammatory response, shock, organ failure and death in humans or animals.

Without wishing to be bound by any particular theory, it is believed that the overall positive charge on certain antimicrobial peptides may assist them to form strong electrostatic interactions with the negatively charged LPS in the membrane of Gram-negative bacteria neutralizing the overall negative charge. The binding of such peptides with LPS of Gram-negative bacteria can have a major effect on the stability of bacterial membranes. Several cationic antimicrobial peptides including LL-37, SMAP-29, and CAP18 can bind LPS. Some antimicrobial peptides can reduce the host immune response to LPS by binding and sequestering it.

In one aspect, the present invention provides a method for treating or preventing endotoxemia in a subject. The method comprises administering to the subject an amount of a peptide disclosed herein effective to bind to an endotoxin so as to treat or prevent endotoxemia in the subject. In one embodiment, the peptide comprises the amino acid sequence of SEQ ID NO:1, 2, 3, 4, 5, 6, 7, or 8.

In some embodiments, the endotoxemia is associated with endotoxin related shock including, but not limited to, septic shock, bacteremia-induced shock, and circulatory shock induced by endotoxin.

In other embodiments, the peptide binds to the endotoxin it encounters in the subject, thereby forming a conjugate that has reduced toxicity and pathogenicity relative to unconjugated endotoxin.

In one embodiment, the peptide binds to the endotoxin it encounters in the subject but does not cause bacterial lysis so as to prevent endotoxin-induced lethality.

In other embodiments, the peptide is covalently or non-covalently attached onto a surface of an invasive device, wherein the endotoxin contacts the peptide on the surface of the device during or following an invasive procedure carried out on the subject.

In one embodiment, the device is a surgical tool.

In another embodiment, the device is an implant.

In other embodiments, the device is a catheter, a staple, a suture, an implant, or a tubing.

In some embodiments, the endotoxin is a LPS of a Gram-negative bacterium.

In another embodiment, the bacterium is of the genus *Klebsiella, Francisela, Acinetobacter, Pseudomonas,*

*Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterium is *Klebsiella pneumoniae, Klebsiella oxytoca, Francisela tularensis, Acinetobacter baumannii, Pseudomonas aeruginosa, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterium is *Klebsiella pneumoniae.*

In other aspects, a device coated with a peptide disclosed herein. In one embodiment, the peptide comprises the amino acid sequence of SEQ ID NO:1, 2, 3, 4, 5, 6, 7, or 8.

In one embodiment, the device is a surgical tool.

In another embodiment, the device is an implant.

In other embodiments, the device is a catheter, a staple, a suture, an implant, or a tubing.

In another aspect, the present invention provides a method for determining lipopolysaccharide (LPS) in a sample. The method comprises contacting the sample with a peptide disclosed herein under a condition such that the LPS binds to the peptide to form a complex; and detecting the complex. In one embodiment, the peptide comprises the amino acid sequence of SEQ ID NO:1, 2, 3, 4, 5, 6, 7, or 8.

In one embodiment, the sample is a biological fluid sample obtained from the subject.

In another embodiment, the sample comprises serum, urine, blood, tissue extractor sputum.

In some embodiments, the sample comprising the LPS is transferred onto a suitable support under a condition permitting LPS in the sample to attach to the support prior to contacting the sample with the peptide.

In another embodiment, the peptide comprises a detectable label.

In some embodiments, the label comprises a fluorescent moiety, a radioactive moiety, or an enzyme.

In other aspects, the present invention provides a method for diagnosing a LPS-associated disorder in a subject. The method comprises forming a complex between LPS and a peptide disclosed herein under a condition such that the LPS binds to the peptide to form the complex; and detecting the complex. In one embodiment, the peptide comprises the amino acid sequence of SEQ ID NO:1, 2, 3, 4, 5, 6, 7, or 8.

In some embodiments, the endotoxin is a LPS of a Gram-negative bacterium.

In another embodiment, the bacterium is of the genus *Klebsiella, Francisela, Acinetobacter, Pseudomonas, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterium is *Klebsiella pneumoniae, Klebsiella oxytoca, Francisela tularensis, Acinetobacter baumannii, Pseudomonas aeruginosa, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterium is *Klebsiella pneumoniae.*

In one embodiment, the LPS is present in a sample obtained from the subject.

In another embodiment, the method further comprises obtaining a sample from the subject and detecting the complex in the sample.

In one embodiment, the sample is a biological fluid sample obtained from the subject.

In another embodiment, the sample comprises serum, urine, blood, tissue extractor sputum.

In some embodiments, the sample comprising the LPS is transferred onto a suitable support under a condition permitting LPS in the sample to attach to the support prior to contacting the sample with the peptide.

In another embodiment, the peptide comprises a detectable label.

In some embodiments, the label comprises a fluorescent moiety, a radioactive moiety, or an enzyme.

In other aspects, the present invention provides a method for treating a composition comprising a LPS. The method comprises contacting the composition with a peptide disclosed herein under a condition such that the LPS binds to the peptide to form a complex; and separating the complex from the composition, thereby reducing or eliminating the LPS from the composition.

In one embodiment, the peptide comprises the amino acid sequence of SEQ ID NO:1, 2, 3, 4, 5, 6, 7, or 8.

In one embodiment, the composition is for parenteral administration.

In another embodiment, the composition is for oral, intravenous, intramuscular, or subcutaneous administration.

In some embodiments, the composition is a cell culture reagent.

In other embodiments, the composition is blood, plasma, serum, or bone marrow.

In some embodiments, the endotoxin is a LPS of a Gram-negative bacterium.

In another embodiment, the bacterium is of the genus *Klebsiella, Francisela, Acinetobacter, Pseudomonas, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterium is *Klebsiella pneumoniae, Klebsiella oxytoca, Francisela tularensis, Acinetobacter baumannii, Pseudomonas aeruginosa, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterium is *Klebsiella pneumoniae*.

The invention will be further described in the following examples, which do not limit the scope of the invention described in the claims.

EXAMPLES

Example 1

Materials and Methods
Bacteria Strain and Growth Conditions

*Klebsiella pneumoniae* ATCC BAA-1705 was purchased from the American Type Culture Collection (Manassas, VA) and grown in Cation-Adjusted Mueller Hinton Broth. Bacteria were aliquoted and frozen at −80° C. with 20% glycerol and enumerated via serial dilution and plating prior to experimentation.

Peptide Synthesis

All peptides were synthesized to order by ChinaPeptides, Inc (Shanghai, China) using Fmoc chemistry. Peptides were provided at >95% purity, with their purity and sequences being confirmed via tandem mass spectrometry using an Orbitrap Fusion Tribrid mass spectrometer (Thermo Scientific). Peptides are provided and used as TFA salts. Sequences and physico-chemical properties are shown in Table 1.

TABLE 1

Sequences and physico-chemical properties of peptides.

| Peptide Name | Sequence | Molecular Weight (APD3) | Hydrophobic residue % (APD3) | PI | Hydrophobic Moment | GRAVY (APD3) | Charge (APD3) |
|---|---|---|---|---|---|---|---|
| *Putative Komodo cathelicidin* | | | | | | | |
| VK-CATH4.1 | FRWRRFFRKAKRFLKRHGVSIAIGTVRLLRRFG (SEQ ID NO: 1) | 4133.019 | 45% | 13.01 | 0.401 | −0.3818 | (+) 12 |
| VK-CATH4.2 | RRWRRFFQKAKRFVKRHGVSIAVGAYRIIG (SEQ ID NO: 2) | 3660.383 | 43% | 12.51 | 0.429 | −0.473 | (+) 10 |
| *Synthetic peptides* | | | | | | | |
| DRGN-2 | FRWRRFFRKAKRFLKRHAVSIAIGTVRLLRRFG (SEQ ID NO: 4) | 4147.046 | 48% | 13.01 | 0.407 | −0.315 | (+) 12 |
| DRGN-3 | Ac-FRWRRFFRKAKRFLKRHAVSIAIGTVRLLRRFG-NH₂ (SEQ ID NO: 4 with N-terminus acetylated and C-terminus amidated) | 4187.095 | N/T | 14 | N/T | N/T | (+) 12 |
| DRGN-4 | FRWRRFFRKAKRFLKRHGVSIAIGTVRLLRRFG-NH₂ (SEQ ID NO: 1 with N-terminus acetylated) | 4174.048 | N/T | 14 | N/T | N/T | (+) 13 |
| DRGN-5 | Ac-FRWRRFFRKAKRFLKRHGVSIAIGTVRLLRRFG-NH₂ (SEQ ID NO: 1 with N-terminus acetylated and C-terminus amidated) | 4173.068 | N/T | 14 | N/T | N/T | (+) 12 |
| DRGN-6 | RRWRRFFQKAKRLLRRFG (SEQ ID NO: 6) | 2477.997 | 38% | 12.88 | 0.750 | −1.461 | (+) 9 |
| DRGN-7 | RRWRRFFQKAKRLLRRFG-NH₂ (SEQ ID NO: 6 with N-terminus acetylated) | 2519.026 | N/T | 14 | N/T | N/T | (+) 10 |
| DRGN-8 | RRWRRFFRKAKRLLRRFG (SEQ ID NO: 7) | 2506.054 | 38% | 12.95 | 0.789 | −1.516 | (+) 10 |
| DRGN-9 | RRWRRFFRKAKRLLRRFG-NH₂ (SEQ ID NO: 7 with N-terminus acetylated) | 2505.074 | N/T | 14 | N/T | N/T | (+) 11 |
| DRGN-10 | RRWRRFFRKAKRIIG (SEQ ID NO: 8) | 2046.501 | 40% | 12.81 | 0.762 | −1.313 | (+) 8 |
| DRGN-11 | RRWRRFFRKAKRIIG-NH₂ (SEQ ID NO: 8 with N-terminus acetylated) | 2045.521 | N/T | 14 | N/T | N/T | (+) 9 |
| *Control and other peptides* | | | | | | | |
| NA-CATH | KRFKKFFKKLKNSVKKRAKKFFKKPKVIGVTFPF (SEQ ID NO: 9) | 4175.26 | 38% | 12.34 | 0.457 | N/T | (+) 15 |
| LL-37 | LLGDFFRKSKEKIGKEFKRIVQRIKDFLRNLVPRTES (SEQ ID NO: 10) | 4493.28 | 35% | 11.15 | 0.521 | N/T | (+) 6 |
| DRGN-1 | PSKKTKPVKPKKVA (SEQ ID NO: 11) | 1535.95 | 21% | 11.2 | 0.013 | −1.393 | (+) 6 |

PI or isoelectric point, GRAVY or "Grand Average of Hydropathy" measuring overall hydrophilicity (negative values) or hydrophobicity (positive values).

CLSI Protocol for MIC

The minimum inhibitory concentration (MIC) of the peptides was determined according to Clinical & Laboratory Standards Institute (CLSJ) guidelines. Bacteria were grown overnight on Cation-adjusted Mueller Hinton Agar (BD 211438, CAMHA) at 37° C. Assays were performed in Cation-adjusted Mueller Hinton Broth (BD 212322, CAMHB) in polypropylene 96 well plates (Corning 3879). Each experiment was performed with three replicates at least three times.

DiSC$_3$5 Assay

Membrane depolarization was measured using DiSC3(5) (3,3'-dipropylthiadicarbocyanine iodide) as previously described with some modifications. Stocks of enumerated frozen *Klebsiella pneumonia* ATCC BAA-1705 were pelleted and washed twice in phosphate buffered saline (PBS) and then resuspended to 4×107 CFU/ml in PBS containing 50 µg/ml DiSC3(5). One hundred µl of this suspension was added to wells of a black 96 well polypropylene plate. The plate was incubated in a fluorescence spectrophotometer (Tecan Infinite 200) and monitored until fluorescence stopped decreasing. One hundred µl of various concentrations of peptide in PBS were added to each well. Bacteria without peptide and peptide without bacteria served as controls. Plate was immediately returned to the spectrofluorometer. Readings were taken at 20 minutes after addition of peptide (excitation=635 nm; emission=670 nm). The experiment was performed with three replicates twice.

EtBr Assay

The ethidium bromide assay was performed as previously described with some modifications. *Klebsiella pneumonia* ATCC BAA-1705 was grown overnight on cation-adjusted Mueller Hinton agar plates at 37° C. Isolated colonies were collected and suspended in PBS, centrifuged and washed with PBS, then adjusted to an OD600 nm of 0.1 in PBS. 180 µL of bacteria were added to 10 µL ethidium bromide (10 mM final concentration) and 10 µL peptide in various concentrations. The Excitation and emission wavelengths were set at 530 and 590 nm, respectively. The increase in fluorescence was then measured 20 minutes after the addition of peptides using a fluorescence spectrophotometer (Tecan Infinite 200). The experiment was performed with three replicates twice.

Hemolysis Assay

Hemolytic activities of the peptides were determined using a solution of 2% sheep erythrocytes (Hemostat Laboratories, LLC) in an assay adapted to a microtiter plate format. Defibrinated sheep's blood was centrifuged at 2000×g and washed three times with PBS. The wash red blood cells were then resuspended up to their original volume and then diluted to a 2% concentration. 2% erythrocytes were combined with various concentrations of peptides. Sterile deionized water was used as 100% hemolysis and PBS was used as 0% hemolysis. The plate was then incubated at 37° C. for one hour. It was then centrifuged at 1000×g for two minutes. The supernatant was then transferred to a fresh flat-bottomed plate and read at OD540 nm. The percent Hemolysis was calculated as the ratio of the experimental well and averaged 100% hemolysis, with the absorbance of averaged 0% hemolysis subtracted from each. The experiment was performed three times with three replicates.

Circular Dichroism Spectroscopy

Circular dichroism (CD) analysis of the peptides was performed using a Jasco J-1500 spectropolarimeter. 100 µg/mL of peptide was used in each experiment. Samples were allowed to equilibrate for 5 min prior to data collection at 25° C. in a 1 mm path length cuvette. Spectra were collected from 190 to 260 nm with at 20 nm/min, a data integration time of 4 seconds and a 1 nm bandwidth. Data shown represents the average of four spectra. The peptides were analyzed in 10 mM sodium phosphate buffer (6.12 mM sodium monohydrogen phosphate heptahydrate; 3.92 mM monosodium phosphate anhydrous; pH 7.4), 50% (v/v) trifluoroethanol (TFE) in phosphate buffer, or 60 mM sodium dodecyl sulfate (SDS) in phosphate buffer. Percent contribution to secondary structure was measured using methods described in Raussens, V. et al. (Analytical Biochemistry, 319(1):114-21 (2003)).

Waxworm Infection Model

*Galleria mellonella* larvae were obtained from Vanderhorst Wholesale (Saint Marys, OH, USA). 10 larvae weighing between 250 and 300 mg were randomly assigned to each group. Waxworms were injected with 10 µL containing 5×10≡CFU suspended in DPBS in their rear left proleg. The waxworms were then allowed to recover for 30 minutes at 37° C. They were then injected with 10 µL DPBS containing the various treatments into their rear right proleg. They were then kept at 37° C. and scored for survival every 24 hours.

Example 2

Peptide Design and Properties

For cathelicidins the predicted cathelin-domain includes the requisite four cysteines (van Hoek, M. L., et al., The Komodo dragon (*Varanus komodoensis*) genome and identification of innate immunity genes and clusters, BMC Genomics, 20(1):684 (2019), which is herein incorporated by reference in its entirety). In addition, the sequence "VTR" is present within 10 amino acids of the last cysteine proposed to be the cleavage site of reptiles. Specifically, these efforts yielded genes and predicted peptide sequences for two potential active cathelicidin peptides, VK-CATH4.1 and VK-CATH4.2 (Table 1), which in the present study have been chemically synthesized and their antibacterial activity against carbapenem-resistant *Klebsiella pneumoniae* (CRKP) was assessed. For VK-CATH4.1 a peptide of 33 amino acids was predicted with a net charge of +12.

When analyzed in the Antimicrobial Peptide Database, the amino acid sequence of the peptide, VK-CATH4.2, that follows the "VTR" sequence is 30 amino acids in length, would have a net +10 charge, and is predicted to be helical. This peptide demonstrates some homology to other known antimicrobial peptides in the Antimicrobial Peptide Database APD3. Thus, this candidate peptide has many of the hallmark characteristics of a potential cathelicidin peptide.

Figure 1B:
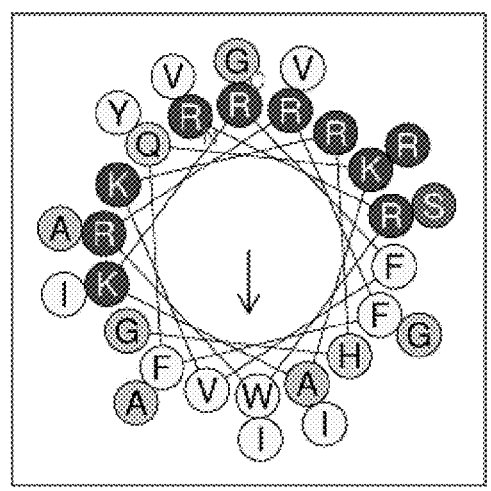
Figure 1B:
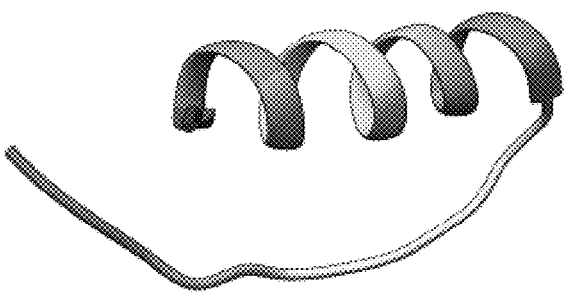
Figure 1C:
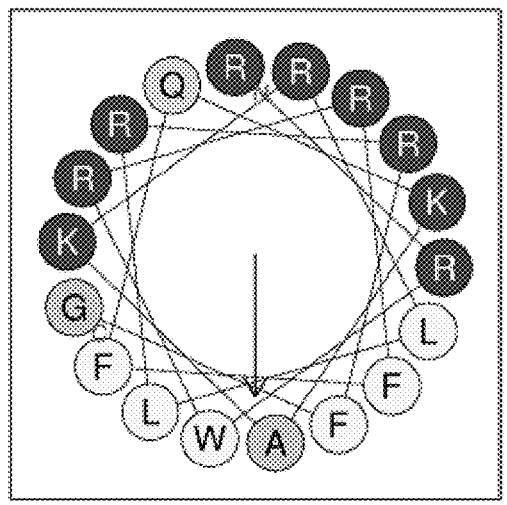
Figure 1C:
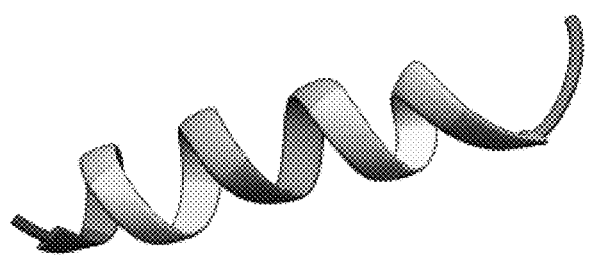
Figure 1D:
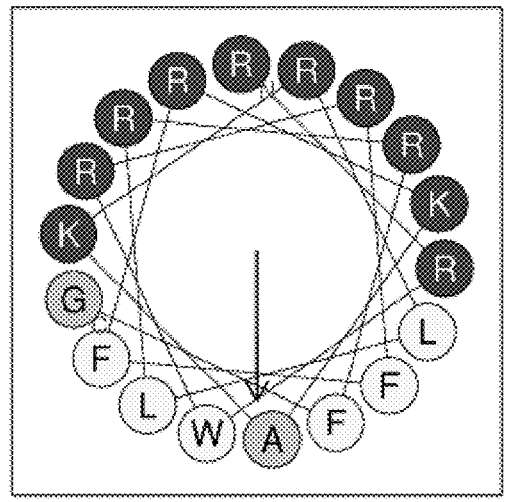
Figure 1D:
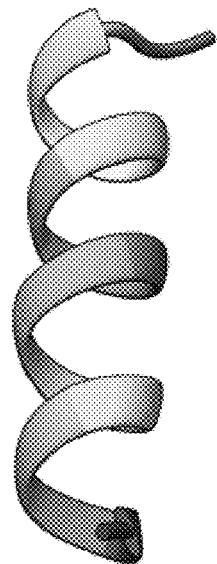
Figure 1E:
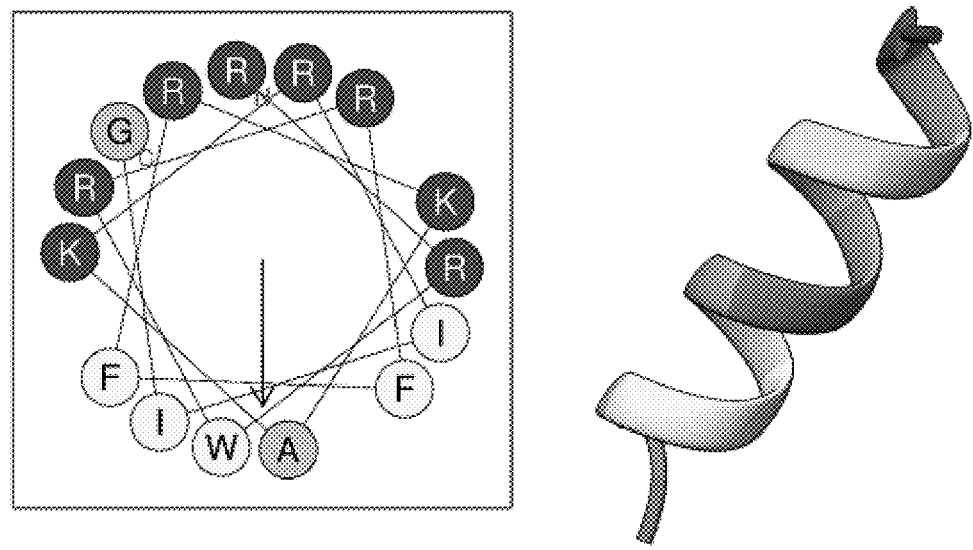

The I-Tasser predicted structure of VK-CATH 4.1 and VK-CATH 4.2 active peptides are shown in FIG. 1A and FIG. 1B. A rational design approach has been applied to the putative Komodo dragon cathelicidin sequences in order to generate a series of novel synthetic peptide derivatives (Table 1).

CRKP is often highly resistant to multiple antibiotics including all beta-lactams, fluoroquinolones and aminoglycosides. To investigate the ability of a library of novel, synthetic antimicrobial peptides against CRKP, we performed minimum inhibitory concentration (MIC) assays according to CLSI standards. Many CAMPs are unable to function in "high salt" environments, including LL-37, which was confirmed for CRKP. LL-37 demonstrated very little antibacterial activity against CRKP under these test conditions (Table 2).

TABLE 2

MIC activity of the peptides against carbapenem-resistant
*K. pneumoniae* strain (ATCC BAA-1705).

| Peptide Name | MIC (µg/mL) | MIC (µM) |
|---|---|---|
| VK-CATH4.1 | 32 | 7.7 |
| VK-CATH4.2 | 32 | 8.7 |
| DRGN-2 | 32 | 7.7 |
| DRGN-3 | 32 | 7.6 |
| DRGN-4 | 32 | 7.7 |
| DRGN-5 | 32 | 7.7 |
| DRGN-6 | 4 | 1.6 |
| DRGN-7 | 4 | 1.6 |
| DRGN-8 | 8 | 3.2 |
| DRGN-9 | 16 | 6.4 |
| DRGN-10 | >64 | >31 |
| DRGN-11 | >64 | >31 |
| NA-CATH | 8 | 1.9 |
| LL-37 | >64 | >14 |
| Colistin | 4 | 3.46 |

MIC was determined following CLSI protocol in CA-MHB (CLSI. Methods for Dilution Antimicrobial Susceptibility Tests for Bacteria That Grow Aerobically Approved Standard—Tenth Edition. Wayne, PA: Clinical and Laboratory Standards Institute; 2015).

The proposed Komodo dragon cathelicidin peptides VK-CATH4.1 and VK-CATH4.2 along with designed synthetic peptide variants were tested for their antimicrobial activity in Cation adjusted Mueller Hinton Broth (CA-MHB), which contains a relatively high concentration of divalent cations. The predicted cathelicidin VK-CATH4.1 showed relatively low activity with a MIC of 32 µg/mL against CRKP, as did the predicted VK-CATH4.2. By contrast, the Naja atra cathelicidin NA-CATH showed a MIC of 8 µg/mL.

We designed a series of novel synthetic peptides which we named DRGN (read "dragon") to reflect that they were inspired by the Komodo dragon peptides and to test different hypotheses about the different regions of VK-CATH4.1 and VK-CATH4.2. The peptides, DRGN-2, DRGN-3, DRGN-4 and DRGN-5 were designed as shown in Table 1 and tested. The peptide DRGN-2 was derived from VK-CATH4.1 by replacing the glycine residue at position 18 of the wild-type sequence with alanine in order to increase the helical propensity of the peptide. In DRGN-3 the N-terminal amine of DRGN-2 is acetylated and its C-terminal carboxy group is amidated in order to reduce susceptibility to proteolytic degradation. These modifications, however, had no significant impact on antimicrobial activity showing little to no positive contribution from the glycine to alanine substitution nor from capping of the N- and C-termini.

DRGN-4 is identical to VK-CATH-4.1 except its C-terminus is amidated in order to increase the overall charge of the peptide. In DRGN-5, the N-terminal amine is acetylated and C-terminus amidated. Both of these peptides showed no discernible increase in antimicrobial effectiveness, again suggesting these N- and C-terminal modifications do not significantly impact activity.

NA-CATH contains two imperfect copies of the 11 amino acid motif ATRA in the first half of the peptide, which were found to be critical to its antibacterial activity. The first copy is termed ATRA1 with the second copy termed ATRA2 We designed a more active peptide by replacing the ATRA2 domain with another copy of the ATRA1 domain, suggesting that different parts (domains) of natural peptides could be combined improve their activity. We have employed a similar approach in designing the peptide DRGN-6, which combines elements from the sequences of VK-CATH4.1 and VK-CATH4.2. DRGN-6 is an eighteen-residue peptide. The N-terminal 12-residue segment of DRGN-6 comes from VK-CATH4.2, representing the helical domain, while the C-terminal 6 residues of DRGN-6 come from VK-CATH4.1 (amino acids 28-33), also representing the highly helical region of that protein. This strategy affords a shorter synthetic peptide that is predicted to be helical and much more strongly amphipathic than either of the parent peptides as shown in the helical wheel projection (FIG. 1) and hydrophobic moment calculations (Table 1).

Three additional peptides (DRGN-7, DRGN-8 and DRGN-9) were generated based on the sequence of DRGN-6. These peptides were designed to assess how increases in net peptide positive charge would impact antibacterial activity. These changes to the DRGN-6 sequence included replacing the neutral polar glutamine residue at position 8 with a cationic basic arginine residue as well as elimination of the negatively charged C-terminal carboxylate group with a carboxamide (Table 1). It has been suggested that the cationic character of an antimicrobial peptide influences its antimicrobial potency. The sequence of the peptide DRGN-7 is identical to that of DRGN-6, however in DRGN-7 the C-terminal carboxyl group of DRGN-6 has been replaces replaced with a carboxamide. This modification effectively increases the net cationic character of the peptide without introducing new basic residues. In DRGN-8, the glutamine residue at position eight was replaced with an arginine further increasing the net charge. Assuming that DRGN-6 adopts a helical conformation, the basic residues are localized to one face of the helix with the glutamine at position eight residing on the cationic face of the helix. Thus, replacing it with a basic residue, such as arginine, should provide a means of increasing net charge that is consistent with the existing predicted polarity of the helical peptide. Finally, DRGN-9 combines the changes introduced in DRGN-7 and -8 to increase cationic character in one peptide, resulting in a greater increase in net positive charge. When the Q in DRGN-6 was switched to an arginine in DRGN-8 and DRGN-9, the MIC values for these peptides increased 2 to 4-fold, contrary to our prediction of increased antibacterial activity with increased cationicity. However, the C-terminal amidation of DRGN-7 had no effect on MIC compared to its unmodified counterpart, DRGN-6, while this same C-terminal amidation to DRGN-9 resulted in a 2-fold increase in MIC (decreased effectiveness) compared to its unmodified counterpart, DRGN-8.

A second pair of truncated peptides, DRGN-10 and DRGN-11, were designed to incorporate the N-terminal helical region of VK-CATH4.2 (amino acids 1-12) and the three C-terminal residues of VK-CATH4.2 (amino acids 28-30). The strategy used to design the DRGN-10 and DRGN-11 peptides is analogous to that which was used to generate DRGN-8 and DRGN-9 respectively. However, in DRGN-10 and DRGN-11 we replaced the C-terminal six-residue sequence LLRRFG (SEQ ID NO: 12) from VK-CATH4.1 with the three-residue sequence IIG from VK-CATH4.2. As was in DRGN-7 and DRGN-9, the C-terminal carboxylate in DRGN-11 has been amidated as opposed to DRNG-10. The DRGN-10 and DRGN-11 peptide variants were prepared in order to probe whether the specific C-terminal sequences of VK-CATH4.1, VK-CATH-4.2 and designed variants were uniquely significant in influencing antibacterial performance. As can be seen from Table 2, DRGN-10 and DRGN-11 peptides were both ineffective against CRKP (MIC>64) suggesting that the sequence LLRRFG (SEQ ID NO: 12) from VK-CATH4.1 is critical for antimicrobial activity of the DRGN-6 peptide. Furthermore, we conclude that C-terminal amidation provided no positive contribution to antibacterial activity.

In summary, some of the VK-CATH chimeric peptides demonstrated significantly improved antimicrobial activity against CRKP relative to the parental peptides. DRGN-6, -7, -8 and -9, all of which contain the N-terminal helical region of VK-CATH4.2 connected to the C-terminal helical region of VK-CATH4.1 (FIG. 1), displayed higher activity compared to either of the parent peptides. The peptides containing the N-terminal and C-terminal helical regions of VK-CATH4.2 (DRGN-10 and DRGN-11) both had MICs greater than the range tested, thus were determined to be virtually inactive. Combining the N-terminal region of VK-CATH4.2 coupled to a C-terminal helical region of VK-CATH4.1 led to the most active peptide in this series. This most active peptide was analyzed for its overall helicity below.

Our results showed that peptides with higher antimicrobial activity such as DRGN-6 did not score higher in terms of GRAVY score, hydropathy index, PI or net charge suggesting that these physicochemical properties are not the only factors contributing to antimicrobial peptide activity of any one cationic, helical AMP. As is shown by the results of this study, there are sequence motif contributors to activity as well as individual residues.

Example 3

Prediction of Antimicrobial Activity of Designed Peptides Using Different Databases The antimicrobial activity of peptides was then predicted using a number of prediction models (Table 3).

TABLE 3

Antimicrobial Peptide Prediction based on Sequence Analysis.

| Peptide Name | CAMP Prediction Score from $CAMP_{R3}$ | | | AntiBP2 Prediction Score |
| --- | --- | --- | --- | --- |
| | SVM | RF | DA | |
| Komodo putative cathelicidins | | | | |
| VK-CATH4.1 | 0.998: AMP | 0.9345: AMP | 1.000: AMP | 1.067: AMP |
| VK-CATH4.2 | 0.989: AMP | 0.9955: AMP | 0.999: AMP | 0.833: AMP |
| Synthetic peptides | | | | |
| DRGN-2 | 0.999: AMP | 0.932: AMP | 0.999: AMP | 0.876: AMP |
| DRGN-3 | N/P | N/P | N/P | N/P |
| DRGN-4 | N/P | N/P | N/P | N/P |
| DRGN-5 | N/P | N/P | N/P | N/P |
| DRGN-6 | 0.999: AMP | 0.8765: AMP | 0.952: AMP | 0.050: AMP |
| DRGN-7 | N/P | N/P | N/P | N/P |
| DRGN-8 | 1.000: AMP | 0.902: AMP | 0.990: AMP | −0.085: Non-AMP |
| DRGN-9 | N/P | N/P | N/P | N/P |
| DRGN-10 | 0.999: AMP | 0.7355: AMP | 0.957: AMP | −0.009: Non-AMP |
| DRGN-11 | N/P | N/P | N/P | N/P |
| Control peptides | | | | |
| NA-CATH | 0.991: AMP | 0.9615: AMP | 0.998: AMP | 1.000: AMP |
| LL-37 | 0.762: AMP | 0.749: AMP | 0.765: AMP | 1.474: AMP |

In Table 3, using 2 different web-based CAMP prediction applications (CAMPR3 database and AntiBP2) (Waghu, F. H. et al., CAMPR3: a database on sequences, structures and signatures of antimicrobial peptides, Nucleic Acids Res. 2016; 44(D1):D1094-7; Lata, S. et al., AntiBP2: improved version of antibacterial peptide prediction. BMC Bioinformatics, 2010; 11 Suppl 1:S19), each peptide was scored and given a prediction of whether it would have antimicrobial activity (AMP) or not (Non-AMP). The activity of peptides with modified N- and C-termini was not able to be predicted.

All peptides were predicted to be antimicrobial by the $CAMP_{R3}$ database's Support Vector Machine, Random forest and discriminant analysis classifiers. Meanwhile, AntiBP2 predicted all but DRGN-8 and DRGN-10 to be antimicrobial. These predication methods however, were not able to analyze peptides with N- or C-terminal modifications. Given the data in Table 2, which showed only DRGN-6 and 8 to be even somewhat active antimicrobial peptides (MIC<16), it can be seen that these computational predictions have a very poor correlation to laboratory results.

Example 4

Antimicrobial Activity

The most active peptide was DRGN-6, and the other peptides that exhibited significant antibacterial activity were all based on that of DRGN-6, with N-terminal modifications and/or amino acid substitutions such as DRGN-7, DRGN-8, DRGN-9, DRGN-10 and DRGN-11 (Table 2). This suggests that the DRGN-6 sequence is a dominant contributor to the antimicrobial activity observed for the whole suite of related peptides. The modifications that were made only reduced the antimicrobial activity of DRGN-6. In particular, DRGN-9 illustrates that the last 6 AA of DRGN-6 are important to its' antimicrobial activity. Based on these studies, a new library of peptides will be designed, starting with DRGN-6 and aiming to preserve or improve upon its helicity and amphipathicity for future study.

We compared the sequence of DRGN-6 to known peptides that are deposited in APD3. It did share limited similarity with a number of peptides, roughly forty percent similarity to cathelicidins from *Python bivittatus*, *Sarcophilus harrisii*, and *Chelonia mydas*. This showed that our designed peptides were distinct and original from natural peptides.

Example 5

Effects on Membrane Permeability and Hyperpolarization

Figure 2A:
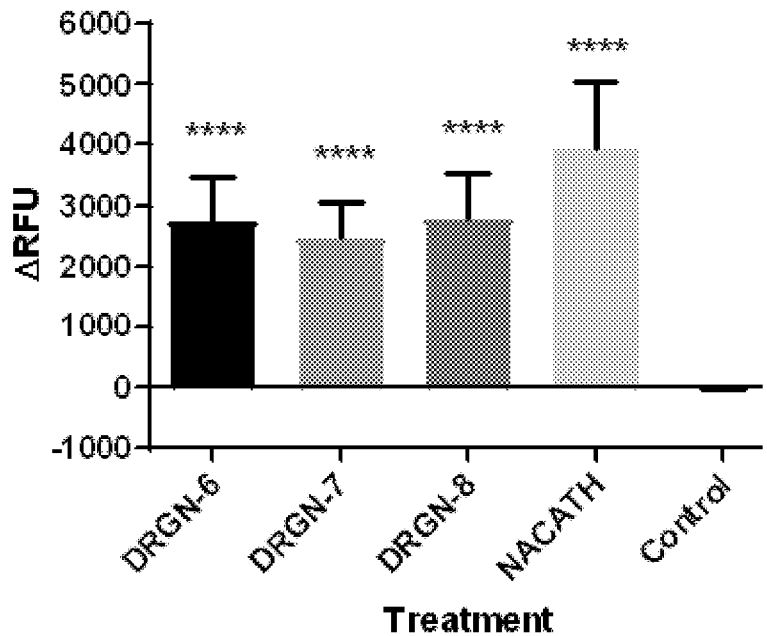
FIGS. 2A-2B are graphs showing (A) membrane disruption as measured by ethidium bromide uptake against $K.$ $pneumoniae$ strain ATCC BAA-1705 in PBS at 50 µg/ml. Δ RFU shown is after 20 min incubation, done twice in triplicate. A one-way ANOVA with multiple comparisons was performed to determine statistical significance (* $p<0.05$;  $p<0.01$; * $p<0.001$); and (B) membrane depolarization Membrane depolarization was measures using 3,3'-dipropylthiadicarbocyanine iodide (DiSC3(5)) against $K.$ $pneumoniae$ strain ATCC BAA-1705 in PBS at 100, 10 and 1 µg/ml. Δ RFU shown is after 20 min incubation, done twice in triplicate. DRGN-6 refers to SEQ ID NO:6, DRGN-7 refers to SEQ ID NO:6 with N-terminus acetylated, DRGN-8 refers to SEQ ID NO:7, NACATH refers to SEQ ID NO:9.
Figure 2B:
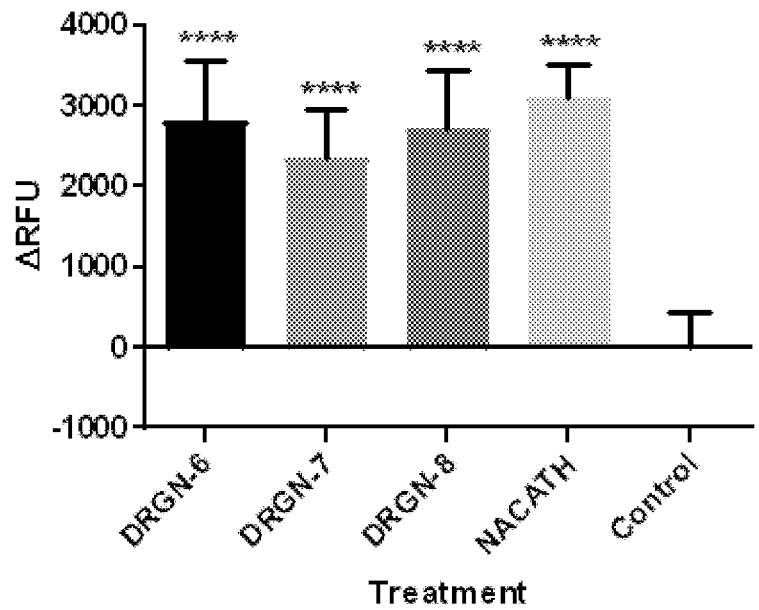

To measure the effects of the most active peptides on *Klebsiella pnuemoniae*'s membrane, two assays were performed. Ethidium Bromide (EtBr) was used to measure permeabilization of the membrane and Dipropylthiadicarbocyanine Iodide ($DiSC_3(5)$) was used to measure depolarization of the membrane. EtBr uptake assays showed that DRGN-6, DRGN-7, and DRGN-8 all caused significant increases in the permeability of the cells (FIG. 2A). ($DiSC_3(5)$) assays showed that DRGN-6, DRGN-7, and DRGN-8 caused significant depolarization at all concentrations tested (FIG. 2B).

Example 6

Hemolysis Assays

Figure 3:
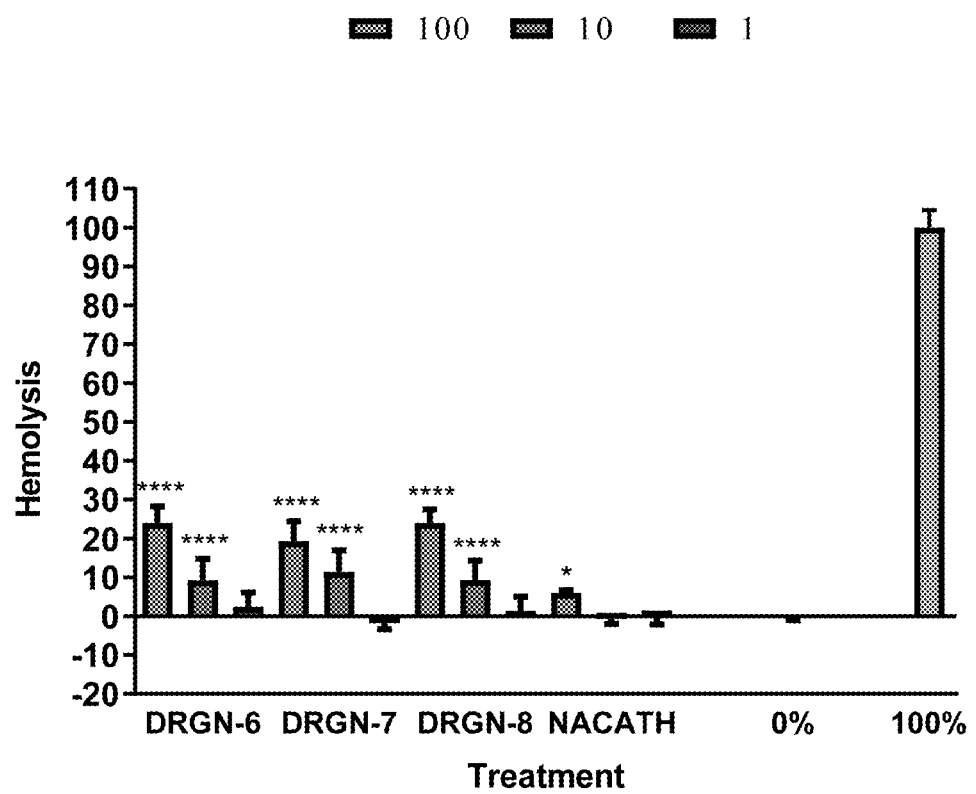
FIG. 3 is a graph showing hemolytic activity against sheep red blood cells. Peptides were tested at 100, 10 and 1 µg/ml. To determine 0% hemolysis, Dulbecco's PBS was added without peptide. To determine 100% hemolysis, sterile deionized water was added without peptide.

Hemolysis assays were performed against 2% sheep's blood and demonstrated that at 100 g/mL there was significant hemolysis of 20-25% in all of the synthetic peptides tested. However, at concentrations closer to their bactericidal concentrations, the peptides showed significantly less hemolysis. At 10 g/mL there was roughly 10% hemolysis in all and at 1 g/mL no significant hemolysis was observed (FIG. 3). This is in comparison to LL-37, which is reported to have hemolysis of less than 10% at greater than 250 µg/ml and NA-CATH which has hemolysis of less than 10% at 100 µg/ml (25).

Example 7

Circular Dichroism (CD) Studies/Secondary Structure

CD spectroscopy was used to ascertain the general secondary structure properties of the most active peptides (DRGN-6, -7 and -8). The secondary structures of many CAMPs are disordered in the absence of anionic membranes or micelles, but adopt more defined secondary structures in their presence. To detect and measure any changes that the DRGN peptides may undergo based on environment, we studied their structural properties in 10 mM phosphate buffer as a negative control, 60 mM SDS in 10 mM phosphate buffer and 50% 2,2,2-Trifluoroethanol (TFE) in 10 mM phosphate buffer. Phosphate buffer without SDS or TFE provided an environment for studying the conformational properties of the peptides structure in the absence a micelle or membrane. Sodium dodecyl sulfate is an anionic surfactant that can form micelles in aqueous buffers mimicking bacterial membranes and simulating the effects an anionic membrane can have on the conformations of antimicrobial peptides. Addition of trifluoroethanol to aqueous buffer promotes increased structure, usually helicity, in peptides with suitable sequences.

In these studies, the structures of both DRGN-6 and DRGN-7 were calculated to contain 70.5% and 72.6% helicity, respectively, in 50% TFE buffer. Interestingly, both showed even greater helical character in SDS buffer (84.2% and 77.0%, respectively). As expected, the CD spectra for both peptides showed little to no helicity in 10 mM phosphate buffer (2.6% and 3.0%, respectively) (Table 4).

TABLE 4

Percent alpha-helicity calculated using method using methods described in (Raussens, V. et al., Protein concentration is not an absolute prerequisite for the determination of secondary structure from circular dichroism spectra: a new scaling method, Analytical Biochemistry, 319(1): 114-21 (2003)).

|  | TFE | SDS | 10 mM phosphate buffer |
|---|---|---|---|
| DRGN-6 | 70.5% | 84.2% | 2.6% |
| DRGN-7 | 72.6% | 77.0% | 3.0% |
| NACATH | 63.5% | 55.6% | 3.4% |

Figure 4A:
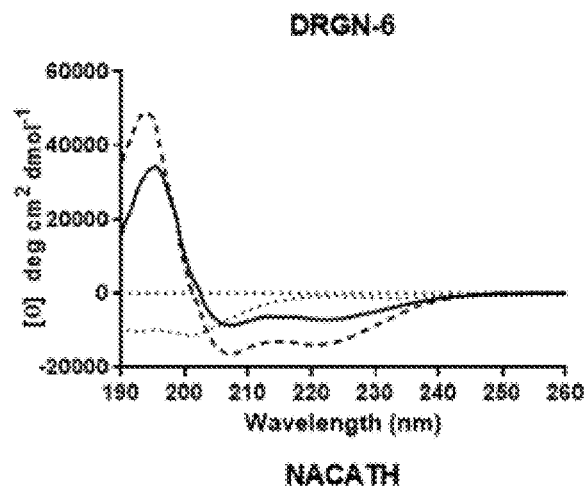
FIGS. 4A-4C are graphs showing circular dichroism (CD) spectra. CD was performed on a Jasco-1500 with (A) DRGN-6 (SEQ ID NO:6), (B) DRGN-7 (SEQ ID NO:6 with N-terminus acetylated), and (C) NACATH (SEQ ID NO:9). All spectra were taken with peptide concentrations of 100 µg/ml in a 1 mm pathway cuvette. Spectra were gathered in 10 mM phosphate buffer (dots), 50% TFE (dashes), and 60 mM SDS (line).
Figure 4B:
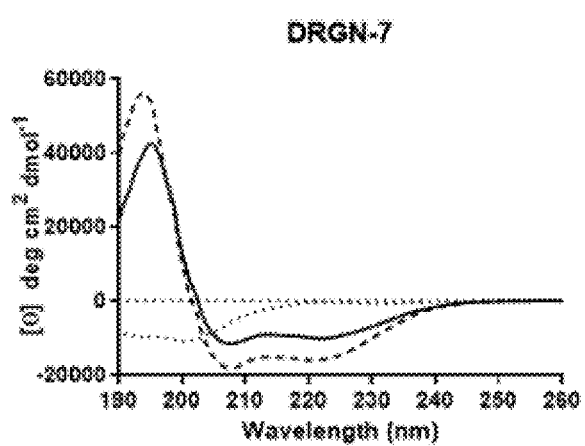
Figure 4C:
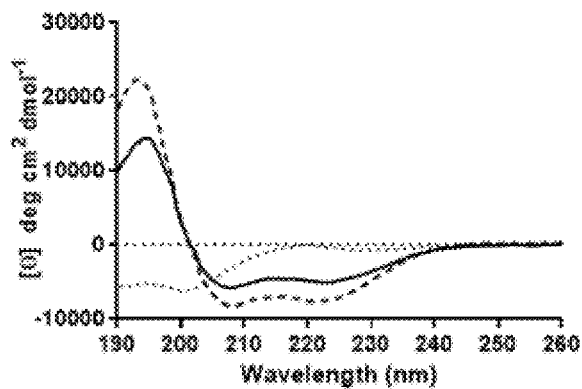

Sequences were submitted to I-TASSER, which predicted that the peptides would have significant helical character, consistent with the CD data (FIG. 4). Helical wheel projections show DRGN-6 and DRGN-8 have a well-structured helical character with a strong amphipathic face (See FIG. 1).

Example 8

Waxworm-Model

Figure 5:
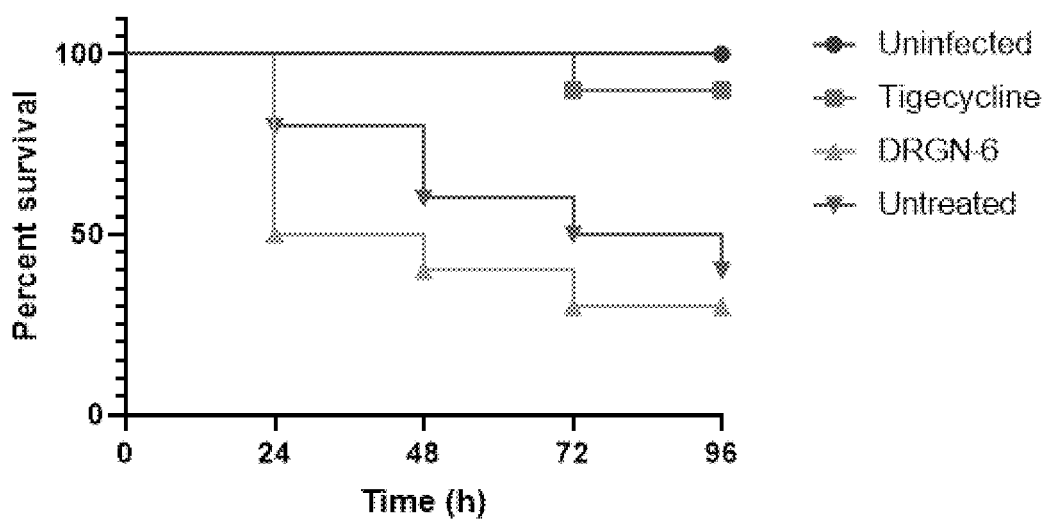
FIG. 5 is a graph showing waxworm survival curves. Waxworms were injected with 10 µL containing $5\times10^5$ CFU in their rear left proleg. The waxworms were allowed to recover for 30 minutes at 37° C. They were injected with 10 µL containing the various treatments. They were kept at 37° C. and scored for survival every 24 hours. Each group contained 10 waxworms.

We tested these antimicrobial peptides in the waxworm, *G. mellonella*. When injected at g per caterpillar, none of the peptides DRGN-6, -7 and -8 alone caused toxicity (data not shown). However, when injected into CRKP infected waxworms, no survival benefit was observed. This suggests that either there was not enough peptide provided in each injection to rescue the infection, or the peptide was not able to reduce the infectious load sufficiently. When the control antibiotic tigecycline was injected, 100% of the caterpillars survived, indicating that it is possible to rescue the waxworms from this infection (FIG. 5).

What is claimed is:

1. A peptide comprising:

(6) RRWRRFFQKAKRLLRRFG (SEQ ID NO: 6);

(7) RRWRRFFRKAKRLLRRFG (SEQ ID NO: 7);

or a variant sequence thereof with one or more substitutions, insertions, additions, or deletions of said peptide; and wherein the C-terminal region of the variant sequence contains LLRRFG (SEQ ID NO: 12) and the variant sequence has at least 80% homology with SEQ ID NO: 6 or SEQ ID NO: 7.

2. The peptide of claim 1, wherein said peptide has a modification at an N- and/or C-terminus of the peptide.

3. The peptide of claim 1, wherein the peptide has a potential to depolarize *Klebsiella pnuemoniae*'s membrane.

4. The peptide of claim 1, wherein the peptide has antimicrobial activity.

5. The peptide of claim 1, wherein MIC activity of the peptide against carbapenem-resistant *K pneumoniae* strain is less than 20 μM.

6. The peptide of claim 5, wherein the MIC activity of the peptide against carbapenem-resistant *K. pneumoniae* strain is less than 10 μM.

7. A composition comprising the peptide of the claim 1.

8. The composition of claim 7, further comprising an excipient.

9. The composition of claim 7 further comprising a molecular crowding agent.

10. The composition of claim 9, wherein the molecular crowding agent comprises polyethylene glycol (PEG), dextran or a hydrophilic polysaccharide.

11. The peptide of claim 1, wherein the peptide reduces biofilm and/or treats endotoxemia.

12. The peptide of claim 1, wherein said peptide comprises:

(a) the amino acid sequence set forth in SEQ ID NO:6; or
   (b) the amino acid sequence set forth in SEQ ID NO:6 with one substitution, insertion, addition, or deletion;
   wherein the peptide further has a modification at the N- and/or C-terminus of the peptide.

13. The peptide of claim 1, wherein said peptide comprises:

(a) the amino acid sequence set forth in SEQ ID NO:7; or
   (b) the amino acid sequence set forth in SEQ ID NO:7 with one substitution, insertion, addition, or deletion;
   wherein the peptide further has a modification at the N- and/or C-terminus of the peptide.

14. The peptide of claim 1, wherein the peptide comprises a detectable label.

15. The peptide of claim 14, wherein the detectable label comprises a fluorescent moiety, a radioactive moiety, or an enzyme.

16. The peptide of claim 1, wherein said peptide has a PI more than 11.15 and up to 14.

17. The peptide of claim 1, wherein said peptide has helicity of more than 70% as measured using 50% 2,2,2-Trifluoroethanol (TFE) buffer via circular dichroism.

18. A peptide comprising a sequence:
Xaa1RWRRFFXaa8KAKRXaa13Xaa14Xaa15Xaa16-Xaa17Xaa18 (SEQ ID NO: 5), wherein independently of each other:
Xaa1 is phenylalanine (F) or arginine (R);
Xaa8 is glutamine (Q) or arginine (R);
Xaa13 is leucine (L) or isoleucine (I);
Xaa14 is leucine (L) or isoleucine (I);
Xaa15 is arginine (R) or glycine (G);
Xaa16 is arginine (R) or absent;
Xaa17 is phenylalanine (F) or absent; and
Xaa18 is glycine (G) or absent;
or a variant sequence thereof comprising one or more substitutions, insertions, additions, or deletions, wherein the variant sequence is at least 80% homologous to SEQ ID NO: 5, and wherein SEQ ID NO: 5 or the variant sequence excludes SEQ ID NO:1.

19. The peptide of claim 18, wherein the variant contains LLRRFG (SEQ ID NO: 12) at the C-terminal region.

20. A peptide comprising:
(1) FRWRRFFRKAKRFLKRHXaa18VSIAIGTVRLL-RRFG (SEQ ID NO:3):
wherein Xaa18 is an amino acid except glycine (G);

(1) FRWRRFFRKAKRFLKRHXaa18VSIAIGTVRLLRRFG (SEQ ID NO: 3):

wherein Xaa18 is an amino acid except glycine (G);

(2) FRWRRFFRKAKRFLKRHAVSIAIGTVRLLRRFG (SEQ ID NO: 4);

or a variant sequence thereof comprising either one or more substitutions, insertions, additions, or deletions, wherein the variant sequence is at least 80% homologous to SEQ ID NO: 3 or SEQ ID NO: 4 and containing LLRRFG (SEQ ID NO: 12) at the C-terminal region and excludes SEQ ID NO:1.

* * * * *

SEQUENCE LISTING

```
<160> NUMBER OF SEQ ID NOS: 12

<210> SEQ ID NO 1
<211> LENGTH: 33
<212> TYPE: PRT
<213> ORGANISM: Artificial Sequence
<220> FEATURE:
<223> OTHER INFORMATION: Peptide

<400> SEQUENCE: 1

Phe Arg Trp Arg Arg Phe Phe Arg Lys Ala Lys Arg Phe Leu Lys Arg
1               5                   10                  15

His Gly Val Ser Ile Ala Ile Gly Thr Val Arg Leu Leu Arg Arg Phe
            20                  25                  30

Gly

<210> SEQ ID NO 2
<211> LENGTH: 30
<212> TYPE: PRT
<213> ORGANISM: Artificial Sequence
<220> FEATURE:
<223> OTHER INFORMATION: Peptide
```

<400> SEQUENCE: 2

Arg Arg Trp Arg Arg Phe Phe Gln Lys Ala Lys Arg Phe Val Lys Arg
1               5                   10                  15

His Gly Val Ser Ile Ala Val Gly Ala Tyr Arg Ile Ile Gly
            20                  25                  30

<210> SEQ ID NO 3
<211> LENGTH: 33
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (18)..(18)
<220> FEATURE:
<221> NAME/KEY: MISC_FEATURE
<222> LOCATION: (18)..(18)
<223> OTHER INFORMATION: Any amino acid other than glycine (G)

<400> SEQUENCE: 3

Phe Arg Trp Arg Arg Phe Phe Arg Lys Ala Lys Arg Phe Leu Lys Arg
1               5                   10                  15

His Xaa Val Ser Ile Ala Ile Gly Thr Val Arg Leu Leu Arg Arg Phe
            20                  25                  30

Gly

<210> SEQ ID NO 4
<211> LENGTH: 33
<212> TYPE: PRT
<213> ORGANISM: Artificial Sequence
<220> FEATURE:
<223> OTHER INFORMATION: Peptide

<400> SEQUENCE: 4

Phe Arg Trp Arg Arg Phe Phe Arg Lys Ala Lys Arg Phe Leu Lys Arg
1               5                   10                  15

His Ala Val Ser Ile Ala Ile Gly Thr Val Arg Leu Leu Arg Arg Phe
            20                  25                  30

Gly

<210> SEQ ID NO 5
<211> LENGTH: 18
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Phenylalanine (F) or Arginine (R)
<220> FEATURE:
<221> NAME/KEY: MISC_FEATURE
<222> LOCATION: (8)..(8)
<223> OTHER INFORMATION: Glutamine (Q) or Arginine (R)
<220> FEATURE:
<221> NAME/KEY: MISC_FEATURE
<222> LOCATION: (13)..(13)
<223> OTHER INFORMATION: Leucine (L) or Isoleucine (I)
<220> FEATURE:
<221> NAME/KEY: MISC_FEATURE
<222> LOCATION: (14)..(14)
<223> OTHER INFORMATION: Leucine (L) or Isoleucine (I)
<220> FEATURE:
<221> NAME/KEY: MISC_FEATURE
<222> LOCATION: (15)..(15)
<223> OTHER INFORMATION: Arginine (R) or Glycine (G)

```
<220> FEATURE:
<221> NAME/KEY: MISC_FEATURE
<222> LOCATION: (16)..(16)
<223> OTHER INFORMATION: Arginine (R) or absent
<220> FEATURE:
<221> NAME/KEY: MISC_FEATURE
<222> LOCATION: (17)..(17)
<223> OTHER INFORMATION: Phenylalanine (F) or absent
<220> FEATURE:
<221> NAME/KEY: MISC_FEATURE
<222> LOCATION: (18)..(18)
<223> OTHER INFORMATION: Glycine (G) or absent

<400> SEQUENCE: 5

Xaa Arg Trp Arg Arg Phe Phe Xaa Lys Ala Lys Arg Xaa Xaa Xaa Xaa
1               5                   10                  15

Xaa Xaa

<210> SEQ ID NO 6
<211> LENGTH: 18
<212> TYPE: PRT
<213> ORGANISM: Artificial Sequence
<220> FEATURE:
<223> OTHER INFORMATION: Peptide

<400> SEQUENCE: 6

Arg Arg Trp Arg Arg Phe Phe Gln Lys Ala Lys Arg Leu Leu Arg Arg
1               5                   10                  15

Phe Gly

<210> SEQ ID NO 7
<211> LENGTH: 18
<212> TYPE: PRT
<213> ORGANISM: Artificial Sequence
<220> FEATURE:
<223> OTHER INFORMATION: Peptide

<400> SEQUENCE: 7

Arg Arg Trp Arg Arg Phe Phe Arg Lys Ala Lys Arg Leu Leu Arg Arg
1               5                   10                  15

Phe Gly

<210> SEQ ID NO 8
<211> LENGTH: 15
<212> TYPE: PRT
<213> ORGANISM: Artificial Sequence
<220> FEATURE:
<223> OTHER INFORMATION: Peptide

<400> SEQUENCE: 8

Arg Arg Trp Arg Arg Phe Phe Arg Lys Ala Lys Arg Ile Ile Gly
1               5                   10                  15

<210> SEQ ID NO 9
<211> LENGTH: 34
<212> TYPE: PRT
<213> ORGANISM: Artificial Sequence
<220> FEATURE:
<223> OTHER INFORMATION: Peptide

<400> SEQUENCE: 9

Lys Arg Phe Lys Lys Phe Phe Lys Lys Leu Lys Asn Ser Val Lys Lys
1               5                   10                  15

Arg Ala Lys Lys Phe Phe Lys Lys Pro Lys Val Ile Gly Val Thr Phe
                20                  25                  30
```

```
Pro Phe

<210> SEQ ID NO 10
<211> LENGTH: 37
<212> TYPE: PRT
<213> ORGANISM: Artificial Sequence
<220> FEATURE:
<223> OTHER INFORMATION: Peptide

<400> SEQUENCE: 10

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 11
<211> LENGTH: 14
<212> TYPE: PRT
<213> ORGANISM: Artificial Sequence
<220> FEATURE:
<223> OTHER INFORMATION: Peptide

<400> SEQUENCE: 11

Pro Ser Lys Lys Thr Lys Pro Val Lys Pro Lys Lys Val Ala
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Peptide

<400> SEQUENCE: 12

Leu Leu Arg Arg Phe Gly
1               5
```